(12) United States Patent
Van et al.

(10) Patent No.: US 10,195,086 B2
(45) Date of Patent: Feb. 5, 2019

(54) TYMPANOSTOMY TUBE DELIVERY DEVICE WITH ROTATABLE

(71) Applicant: Tusker Medical, Inc., Menlo Park, CA (US)

(72) Inventors: Nga K. Van, San Jose, CA (US); Mathew D. Clopp, Santa Clara, CA (US); Scott J. Baron, Menlo Park, CA (US); Thomas D. Gross, Los Gatos, CA (US)

(73) Assignee: Tusker Medical, Inc., Menlo Park, CA (US)

( * ) Notice: Subject to any disclaimer, the term of this patent is extended or adjusted under 35 U.S.C. 154(b) by 0 days.

(21) Appl. No.: 14/456,080

(22) Filed: Aug. 11, 2014

(65) Prior Publication Data

US 2016/0038342 A1 Feb. 11, 2016

(51) Int. Cl.
*A61F 11/00* (2006.01)
*A61B 90/00* (2016.01)

(52) U.S. Cl.
CPC ....... *A61F 11/002* (2013.01); *A61B 2090/038* (2016.02)

(58) Field of Classification Search
CPC .... A61F 11/002; A61F 11/004; A61F 11/006; A61F 11/00; A61B 17/3415; A61B 17/3417; A61B 17/8819; A61B 17/32002; A61B 17/320016; A61B 17/34; A61B 17/3421; A61B 2017/3447; A61B 2017/3443; A61B 2017/3445; A61B 2017/3449; A61B 2017/00477; A61B 2017/00787; A61B 2017/00367; A61B 2017/00389; A61B 2017/00305; A61B 2017/00309; A61B 2017/00331;
(Continued)

(56) References Cited

U.S. PATENT DOCUMENTS 858,673 A 7/1907 Roswell
1,920,006 A 7/1933 Dozier et al.
(Continued)

FOREIGN PATENT DOCUMENTS

CN 86105171 A 3/1987
CN 2635015 Y 8/2004
(Continued)

OTHER PUBLICATIONS

International Search Report and Written Opinion for International Application No. PCT/US2015/044177, dated Oct. 30, 2015.
(Continued)

*Primary Examiner* — Jocelin C Tanner

(57) ABSTRACT

An instrument comprises a shaft assembly, a handpiece body, and a drive assembly. The shaft assembly comprises a plurality of coaxially arranged shafts and a tympanostomy tube. The shaft assembly further includes a flexible section. The shaft assembly extends distally from the handpiece body. The drive assembly is operable to drive the shafts of the shaft assembly in a predetermined sequence to deploy the tympanostomy tube. One or more of the shafts are configured to translate along the flexible section of the shaft assembly as a part of the predetermined sequence to deploy the tympanostomy tube.

21 Claims, 24 Drawing Sheets

(58) Field of Classification Search
CPC ......... A61B 2017/00353; A61B 2017/320032; A61B 2017/3433; A61B 2010/0208; A61B 5/150511; A61M 25/0138
See application file for complete search history.

(56) References Cited

U.S. PATENT DOCUMENTS

| | | |
|---|---|---|
| 2,162,681 A | 6/1939 | Ryan |
| 3,473,170 A | 10/1969 | Haase et al. |
| 3,638,643 A | 2/1972 | Hotchkiss |
| 3,741,197 A | 6/1973 | Sanz et al. |
| 3,807,404 A | 4/1974 | Weissman et al. |
| 3,888,258 A | 6/1975 | Akiyama |
| 3,897,786 A | 8/1975 | Garnett et al. |
| 3,913,584 A | 10/1975 | Walchle et al. |
| 3,948,271 A | 4/1976 | Akiyama |
| 3,991,755 A | 11/1976 | Vernon et al. |
| 4,168,697 A | 9/1979 | Cantekin |
| 4,335,713 A | 6/1982 | Komiya |
| 4,335,715 A | 6/1982 | Kirkley |
| 4,380,998 A | 4/1983 | Kieffer, III et al. |
| 4,406,287 A | 9/1983 | Parker et al. |
| 4,468,218 A | 8/1984 | Armstrong |
| 4,473,073 A | 9/1984 | Darnell |
| 4,552,137 A | 11/1985 | Strauss |
| 4,564,009 A | 1/1986 | Brinkhoff |
| 4,712,537 A | 12/1987 | Pender |
| 4,750,491 A | 6/1988 | Kaufman et al. |
| 4,796,624 A | 1/1989 | Trott et al. |
| 4,800,876 A | 1/1989 | Fox et al. |
| 4,913,132 A | 4/1990 | Gabriel |
| 4,946,440 A | 8/1990 | Hall |
| 4,968,296 A | 11/1990 | Ritch et al. |
| 4,971,076 A | 11/1990 | Densert et al. |
| 5,026,378 A | 6/1991 | Goldsmith, III |
| 5,044,373 A | 9/1991 | Northeved et al. |
| 5,047,007 A | 9/1991 | McNichols et al. |
| 5,053,040 A | 10/1991 | Goldsmith, III |
| 5,092,837 A | 3/1992 | Ritch et al. |
| 5,107,861 A | 4/1992 | Narboni |
| 5,135,478 A | 8/1992 | Sibalis |
| 5,158,540 A * | 10/1992 | Wijay ............... A61M 25/0054 604/101.05 |
| 5,178,623 A | 1/1993 | Cinberg et al. |
| 5,254,120 A | 10/1993 | Cinberg et al. |
| 5,261,903 A | 11/1993 | Dhaliwal et al. |
| D352,780 S | 11/1994 | Glaeser et al. |
| 5,370,656 A | 12/1994 | Shevel |
| 5,421,818 A | 6/1995 | Arenberg |
| 5,466,239 A | 11/1995 | Cinberg et al. |
| 5,489,286 A | 2/1996 | Cinberg et al. |
| 5,496,329 A | 3/1996 | Reisinger |
| D378,611 S | 3/1997 | Croley |
| 5,610,988 A | 3/1997 | Miyahara |
| 5,643,280 A | 7/1997 | Del Rio et al. |
| 5,645,584 A | 7/1997 | Suyama |
| 5,658,235 A | 8/1997 | Priest et al. |
| 5,674,196 A | 10/1997 | Donaldson et al. |
| 5,676,635 A | 10/1997 | Levin |
| 5,681,323 A | 10/1997 | Arick |
| D387,863 S | 12/1997 | Herman et al. |
| 5,707,383 A | 1/1998 | Bays et al. |
| 5,775,336 A | 7/1998 | Morris |
| 5,782,744 A | 7/1998 | Money |
| 5,792,100 A | 8/1998 | Shantha |
| 5,827,995 A | 10/1998 | Del Rio et al. |
| 5,893,828 A | 4/1999 | Uram |
| 5,893,837 A | 4/1999 | Eagles et al. |
| 5,984,930 A | 11/1999 | Maciunas et al. |
| D418,223 S | 12/1999 | Phipps et al. |
| D420,741 S | 2/2000 | Croley |
| 6,022,342 A | 2/2000 | Mukherjee |
| 6,024,726 A | 2/2000 | Hill |
| 6,039,748 A * | 3/2000 | Savage ............ A61B 17/32002 606/107 |
| 6,045,528 A | 4/2000 | Arenberg et al. |
| D424,197 S | 5/2000 | Sydlowski et al. |
| 6,059,803 A | 5/2000 | Spilman |
| D426,135 S | 6/2000 | Lee |
| 6,077,179 A | 6/2000 | Liechty, II |
| 6,110,196 A | 8/2000 | Edwards |
| 6,137,889 A | 10/2000 | Shennib et al. |
| 6,171,236 B1 | 1/2001 | Bonutti |
| 6,183,469 B1 | 2/2001 | Thapliyal et al. |
| 6,200,280 B1 | 3/2001 | Brenneman et al. |
| 6,206,888 B1 | 3/2001 | Bicek et al. |
| 6,245,077 B1 | 6/2001 | East et al. |
| 6,248,112 B1 | 6/2001 | Gambale et al. |
| 6,251,121 B1 | 6/2001 | Saadat |
| 6,258,067 B1 | 7/2001 | Hill |
| D450,843 S | 11/2001 | McGuckin, Jr. et al. |
| 6,319,199 B1 | 11/2001 | Sheehan et al. |
| 6,358,231 B1 | 3/2002 | Schindler et al. |
| 6,398,758 B1 | 6/2002 | Jacobsen et al. |
| 6,416,512 B1 | 7/2002 | Ellman et al. |
| 6,440,102 B1 | 8/2002 | Arenberg et al. |
| 6,447,522 B2 | 9/2002 | Gambale et al. |
| 6,475,138 B1 | 11/2002 | Schechter et al. |
| 6,512,950 B2 | 1/2003 | Li et al. |
| 6,514,261 B1 | 2/2003 | Randall et al. |
| 6,520,939 B2 | 2/2003 | Lafontaine |
| 6,522,827 B1 | 2/2003 | Loeb et al. |
| 6,553,253 B1 | 4/2003 | Chang |
| 6,645,173 B1 | 11/2003 | Liebowitz |
| 6,648,873 B2 | 11/2003 | Arenberg et al. |
| 6,663,575 B2 | 12/2003 | Leysieffer |
| 6,682,558 B2 | 1/2004 | Tu et al. |
| 6,770,080 B2 | 8/2004 | Kaplan et al. |
| 6,916,159 B2 | 7/2005 | Rush et al. |
| 6,962,595 B1 | 11/2005 | Chamness et al. |
| 7,127,285 B2 | 10/2006 | Henley et al. |
| 7,137,975 B2 | 11/2006 | Miller et al. |
| D535,027 S | 1/2007 | James et al. |
| 7,160,274 B2 | 1/2007 | Ciok et al. |
| 7,344,507 B2 | 3/2008 | Briggs et al. |
| 7,351,246 B2 | 4/2008 | Epley |
| 7,381,910 B1 | 6/2008 | Zarbatany et al. |
| D595,410 S | 6/2009 | Luzon |
| 7,563,232 B2 | 7/2009 | Freeman et al. |
| D598,543 S | 8/2009 | Vogel et al. |
| 7,654,997 B2 | 2/2010 | Makower et al. |
| 7,677,734 B2 | 3/2010 | Wallace |
| 7,704,259 B2 | 4/2010 | Kaplan et al. |
| 7,749,254 B2 | 7/2010 | Sobelman et al. |
| D622,842 S | 8/2010 | Benoist |
| D640,374 S | 6/2011 | Liu et al. |
| 8,052,693 B2 | 11/2011 | Shahoian |
| 8,192,420 B2 | 6/2012 | Morriss et al. |
| 8,249,700 B2 | 8/2012 | Clifford et al. |
| 8,282,648 B2 | 10/2012 | Tekulve |
| 8,409,175 B2 | 4/2013 | Lee et al. |
| 8,475,488 B2 | 4/2013 | Clifford et al. |
| 8,498,425 B2 | 7/2013 | Graylin |
| 8,518,098 B2 | 8/2013 | Roeder et al. |
| 8,702,722 B2 | 4/2014 | Shahoian |
| 8,840,602 B2 | 9/2014 | Morriss et al. |
| 8,849,394 B2 | 9/2014 | Clifford et al. |
| 8,864,774 B2 | 10/2014 | Liu et al. |
| 8,998,927 B2 | 4/2015 | Kaplan et al. |
| 9,011,363 B2 | 4/2015 | Clopp et al. |
| 9,023,059 B2 | 5/2015 | Loushin et al. |
| 9,216,112 B2 | 12/2015 | Clifford et al. |
| 9,320,652 B2 | 4/2016 | Andreas et al. |
| 9,387,124 B2 | 7/2016 | Clifford |
| 9,539,146 B2 | 1/2017 | Girotra et al. |
| 9,681,891 B2 | 6/2017 | Andreas et al. |
| 9,707,131 B2 | 7/2017 | Shahoian |
| 9,770,366 B2 | 9/2017 | Liu et al. |
| 9,833,359 B2 | 12/2017 | Clopp |
| 9,833,360 B2 | 12/2017 | Andreas et al. |
| 9,833,601 B2 | 12/2017 | Clifford |
| 2001/0020173 A1 * | 9/2001 | Klumb ............... A61F 2/88 606/194 |
| 2002/0026125 A1 | 2/2002 | Leysieffer |

(56) References Cited

U.S. PATENT DOCUMENTS

| | | |
|---|---|---|
| 2002/0069883 A1 | 6/2002 | Hirchenbain |
| 2002/0111585 A1 | 8/2002 | Lafontaine |
| 2002/0138091 A1 | 9/2002 | Pflueger |
| 2002/0161379 A1 | 10/2002 | Kaplan et al. |
| 2002/0169456 A1 | 11/2002 | Tu et al. |
| 2003/0018291 A1 | 1/2003 | Hill et al. |
| 2003/0040717 A1 | 2/2003 | Saulenas et al. |
| 2003/0060799 A1 | 3/2003 | Arenberg et al. |
| 2003/0187456 A1 | 10/2003 | Perry |
| 2003/0199791 A1 | 10/2003 | Boecker et al. |
| 2004/0054339 A1 | 3/2004 | Ciok et al. |
| 2004/0064024 A1* | 4/2004 | Sommer .............. A61N 1/056 600/374 |
| 2005/0033343 A1 | 2/2005 | Chermoni |
| 2005/0165368 A1 | 7/2005 | Py et al. |
| 2005/0182385 A1 | 8/2005 | Epley |
| 2005/0187546 A1 | 8/2005 | Bek et al. |
| 2005/0235422 A1 | 10/2005 | Wallace |
| 2005/0240147 A1* | 10/2005 | Makower .............. A61B 17/24 604/96.01 |
| 2006/0004323 A1* | 1/2006 | Chang .................. A61B 17/24 604/28 |
| 2006/0095050 A1 | 5/2006 | Hartley et al. |
| 2006/0142700 A1 | 6/2006 | Sobelman et al. |
| 2006/0155304 A1 | 7/2006 | Kaplan et al. |
| 2006/0161218 A1 | 7/2006 | Danilov |
| 2006/0163313 A1 | 7/2006 | Larson |
| 2006/0282062 A1 | 12/2006 | Ishikawa et al. |
| 2007/0088247 A1 | 4/2007 | Bliweis et al. |
| 2007/0233222 A1 | 10/2007 | Roeder et al. |
| 2007/0276466 A1* | 11/2007 | Lavelle .................. A61F 2/04 623/1.22 |
| 2008/0027423 A1 | 1/2008 | Choi et al. |
| 2008/0051804 A1 | 2/2008 | Cottler et al. |
| 2008/0065011 A1 | 3/2008 | Marchand et al. |
| 2008/0212416 A1 | 9/2008 | Polonio et al. |
| 2008/0262468 A1 | 10/2008 | Clifford et al. |
| 2008/0262508 A1 | 10/2008 | Clifford et al. |
| 2008/0262510 A1 | 10/2008 | Clifford |
| 2009/0163828 A1 | 6/2009 | Turner et al. |
| 2009/0171271 A1* | 7/2009 | Webster ............. A61B 17/3417 604/95.01 |
| 2009/0209972 A1 | 8/2009 | Loushin et al. |
| 2009/0299344 A1 | 12/2009 | Lee et al. |
| 2009/0299379 A1 | 12/2009 | Katz et al. |
| 2009/0299433 A1 | 12/2009 | Lee |
| 2010/0041447 A1 | 2/2010 | Graylin |
| 2010/0048978 A1* | 2/2010 | Sing ...................... A61N 5/1016 600/6 |
| 2010/0061581 A1 | 3/2010 | Soetejo et al. |
| 2010/0160819 A1* | 6/2010 | Parihar .............. A61B 10/0275 600/566 |
| 2010/0198135 A1 | 8/2010 | Morriss et al. |
| 2010/0217296 A1 | 8/2010 | Morriss et al. |
| 2010/0274188 A1* | 10/2010 | Chang .................. A61B 1/227 604/96.01 |
| 2010/0324488 A1 | 12/2010 | Smith |
| 2011/0015645 A1* | 1/2011 | Liu .................... A61B 17/3468 606/109 |
| 2011/0022069 A1* | 1/2011 | Mitusina ........... A61B 17/32002 606/180 |
| 2011/0077579 A1 | 3/2011 | Harrison et al. |
| 2011/0288559 A1 | 11/2011 | Shahoian |
| 2012/0179187 A1 | 7/2012 | Loushin et al. |
| 2012/0265097 A1 | 10/2012 | Melchiorri et al. |
| 2012/0283563 A1* | 11/2012 | Moore ............... A61B 10/0275 600/437 |
| 2012/0310145 A1 | 12/2012 | Clifford et al. |
| 2013/0030456 A1 | 1/2013 | Assell et al. |
| 2013/0090544 A1 | 4/2013 | Clifford et al. |
| 2013/0338678 A1* | 12/2013 | Loushin ................ A61F 11/002 606/109 |
| 2014/0094733 A1 | 4/2014 | Clopp et al. |
| 2014/0100584 A1 | 4/2014 | Konstorum et al. |
| 2014/0194891 A1 | 7/2014 | Shahoian |
| 2014/0276906 A1 | 9/2014 | Andreas et al. |
| 2014/0277050 A1 | 9/2014 | Andreas et al. |
| 2015/0142029 A1 | 5/2015 | Fahn et al. |
| 2015/0164695 A1 | 6/2015 | Liu et al. |
| 2015/0209509 A1 | 7/2015 | O'Cearbhaill et al. |
| 2015/0305944 A1 | 10/2015 | Kaplan et al. |
| 2016/0038341 A1 | 2/2016 | Clopp et al. |
| 2016/0045369 A1 | 2/2016 | Clopp |
| 2016/0045370 A1 | 2/2016 | Andreas et al. |
| 2016/0045371 A1 | 2/2016 | Girotra et al. |
| 2016/0213519 A1 | 7/2016 | Andreas et al. |
| 2017/0209310 A1 | 7/2017 | Girotra et al. |
| 2017/0281230 A1 | 10/2017 | Andreas et al. |
| 2018/0055693 A1 | 3/2018 | Liu et al. |
| 2018/0085258 A1 | 3/2018 | Andreas et al. |
| 2018/0085563 A1 | 3/2018 | Clifford et al. |
| 2018/0116876 A1 | 5/2018 | Clopp |

FOREIGN PATENT DOCUMENTS

| | | |
|---|---|---|
| CN | 102920491 A | 2/2013 |
| CN | 103327881 A | 9/2013 |
| DE | 19618585 | 11/1997 |
| DE | 19918288 A1 | 10/2000 |
| EP | 0214527 A1 | 3/1987 |
| FR | 2526656 | 11/1983 |
| JP | H 07-116190 A | 5/1995 |
| WO | WO 1999/011175 A1 | 3/1999 |
| WO | WO 2006/119512 | 11/2006 |
| WO | WO 2008/030485 | 3/2008 |
| WO | WO 2008/036368 | 3/2008 |
| WO | WO 2008/131195 | 10/2008 |
| WO | WO 2009/010788 | 1/2009 |
| WO | WO 2009/105619 | 8/2009 |
| WO | WO 2011/008948 | 1/2011 |
| WO | WO 2014/075949 | 5/2014 |
| WO | WO 2014/143543 | 9/2014 |
| WO | WO 2014/158571 | 10/2014 |
| WO | WO 2016/022899 | 2/2016 |
| WO | WO 2016/025308 | 2/2016 |
| WO | WO 2016/025309 | 2/2016 |
| WO | WO 2016/025310 | 2/2016 |
| WO | WO 2016/025453 | 2/2016 |

OTHER PUBLICATIONS

Rhinology Products, Boston Medical Products, www.bosmed.com [date of publication unknown], pp. 1-16.

Patent Examination Report No. 1 for Australian Patent Application No. 2013209354, dated Oct. 13, 2014, 5 pages.

First Office Action for Chinese Patent Application No. 200880020861.9, dated Jul. 12, 2011, 10 pages.

Second Office Action for Chinese Patent Application No. 200880020861.9, dated Dec. 31, 2011, 3 pages.

Search Report for Chinese Patent Application No. 201310047126.X, dated Mar. 6, 2015, 2 pages.

Second Office Action for Chinese Patent Application No. 201310047126.X, dated Mar. 16, 2015, 10 pages.

Office Action for European Application No. 08746237.0, dated Mar. 24, 2016, 3 pages.

Office Action for European Application No. 08746237.0, dated Aug. 4, 2015, 7 pages.

Supplementary Partial Search Report for European Application No. 08746237.0, dated Jun. 30, 2014, 9 pages.

Notification of Reasons for Refusal for Japanese Patent Application No. 2010-504267, dated Nov. 20, 2012, 4 pages.

Notification of Reasons for Refusal for Japanese Patent Application No. 2010-504267, dated Nov. 12, 2013, 4 pages.

International Search Report for International Application No. PCT/US2008/060779, dated Sep. 3, 2008.

Written Opinion for International Application No. PCT/US2008/060779, dated Sep. 3, 2008.

International Preliminary Report on Patentability for International Application No. PCT/US2008/060779, dated Nov. 17, 2009.

(56) References Cited

OTHER PUBLICATIONS

Office Action for U.S. Appl. No. 11/749,729, dated May 26, 2011, 11 pages.
Office Action for U.S. Appl. No. 11/749,729, dated Jun. 17, 2010, 8 pages.
Office Action for U.S. Appl. No. 11/749,733, dated Jun. 10, 2009, 13 pages.
Office Action for U.S. Appl. No. 11/749,733, dated Dec. 2, 2008, 9 pages.
U.S. Appl. No. 61/085,360, filed Jul. 31, 2008.
International Search Report for International Application No. PCT/US2009/052395, dated Nov. 6, 2009.
Written Opinion for International Application No. PCT/US2009/052395, dated Nov. 6, 2009.
International Search Report for International Application No. PCT/US2010/058718, dated Feb. 17, 2011.
Written Opinion for International Application No. PCT/US2010/058718, dated Feb. 17, 2011.
U.S. Appl. No. 61/225,893, filed Jul. 15, 2009.
Patent Examination Report No. 1 for Australian Application No. 2010273372, dated Nov. 12, 2014, 2 pages.
First Office Action for Chinese Application No. 201080041755.6, dated Jul. 3, 2013.
Notification of Reasons for Refusal for Japanese Application No. 2012-520778, dated Feb. 18, 2014.
Communication of the Substantive Examination Report for Mexican Application No. MX/a/2012/000691, dated Apr. 24, 2014.
International Search Report for International Application No. PCT/US2010/042128, dated Aug. 27, 2010.
Written Opinion International Application No. PCT/US2010/042128, dated Aug. 27, 2010.
International Preliminary Report on Patentability for International Application No. PCT/US2010/042128, dated Jan. 17, 2012.
European Search Report for European Application No. 13173409.7, dated Sep. 16, 2013.
Search Report and Written Opinion for International Patent Application No. PCT/US2015/044179, dated Dec. 18, 2015, 15 pages.
International Search Report and Written Opinion for International Application No. PCT/US2014/018320, dated Jun. 2, 2014, 10 pages.
International Search Report and Written Opinion for International Application No. PCT/US2014/018347, dated Apr. 17, 2014, 9 pages.
International Search Report and Written Opinion for International Application No. PCT/US2015/044173, dated Oct. 12, 2015, 9 pages.
International Search Report and Written Opinion for International Application No. PCT/US2015/044183, dated Nov. 4, 2015, 9 pages.
International Search Report and Written Opinion for International Application No. PCT/US2015/044610, dated Nov. 5, 2015, 12 pages.
International Search Report for International Application No. PCT/US2009/069388, dated Jun. 30, 2010.
Written Opinion for International Application No. PCT/US2009/069388, dated Jun. 30, 2010.
Comeau, M. et al., "Local Anesthesia of the Ear by Iontophoresis," vol. 98, Arch. Otolaryngol., pp. 114-120 (Aug. 1973).
Comeau, M. et al., "Anesthesia of the Human Tympanic Membrane by Iontophoresis of a Local Anesthetic," The Larynogoscope, vol. 88, pp. 277-285 (1978).
Echols, D. F. et al., "Anesthesia of the Ear by Iontophoresis of Lidocaine," Arch. Otolaryngol., vol. 101, pp. 418-421 (Jul. 1975).
Epley, J. M., "Modified Technique of Iontophoretic Anesthesia for Myringotomy in Children," Arch. Otolaryngol., vol. 103, pp. 358-360 (Jun. 1977).
Hasegawa, M. et al., "Iontophorectic anaesthesia of the tympanic membrane," Clinical Otolaryngoloy, vol. 3, pp. 63-66 (1978).
Ramsden, R. T. et al., "Anaesthesia of the tympanic membrane using iontophoresis," The Journal of Laryngology and Otology, 56(9):779-785 (Sep. 1977).
"Definition of Plenum," Compact Oxford English Dictionary [online], Retrieved from the Internet: <http://oxforddictionaries.com/definition/english/plenum>, Retrieved on Aug. 6, 2012, 2 pages.
"Definition of Plenum," Merriam-Webster's Online Dictionary, 11th Edition [online], Retrieved from the Internet: <http://www.merriam-webster.com/dictionary/plenum>, Retrieved on Aug. 14, 2012, 1 page.
Medtronic XOMED, "Activent® Antimicrobial Ventilation Tubes," Rev. 1.1, pp. 1-4, 2002, Jacksonville, FL.
Micromedics Innovative Surgical Products, "Micromedics Tympanostomy Tubes," [online], Retrieved on Jul. 15, 2010, Retrieved from the Internet <URL: http://www.micromedics-usa.com/products/otology/micromedicstubes.htm>, 7 pages.
Armstrong, "A New Treatment for Chronic Secretory Otitis Media" A.M.A. Archives of Otolaryngology, pp. 653-654 (1954).
Feuerstein, "A Split-Tube Prosthesis in Serous Otitis Media" Sixty-ninth Annual Session of the American Academy of Ophthalmology and Otolaryngology, Oct. 18-23, 1964, Chicago, IL, pp. 343-344.
Jurgens. et al., "Three New Middle Ear Ventilation Tubes" Seventy-sixth Annual Session of the American Academy of Ophthalmology and Otolaryngology, Sep. 20-24, 1971, Las Vegas, NV, pp. 1017-1019 (1971).
Lindeman et al., The "Arrow Tube" Residents in Otolaryngology, Massachusetts Eye and Ear Infirmary, 1 page (1964).
Pappas, "Middle Ear Ventilation Tubes" Meeting of the Southern Section of the American Laryngological, Rhinological and Otological Society, Inc., Williamsburg, VA, Jan. 12, 1974, pp. 1098-1117.
Per-Lee, "A Wide Flanged Middle Ear Ventilation Tube" Seventy-first Annual Session of the American Academy of Ophthalmology and Otolaryngology, Oct. 16-21, 1966, Chicago, IL, pp. 358-359.
Reuter, "The Stainless Bobbin Middle Ear Ventilation Tube" Seventy-second Annual Session of the American Academy of Ophthalmology and Otolaryngology, Oct. 29-Nov. 3, 1967, Chicago, IL, pp. 121-122.
Ringenberg, "A New Middle Ear Ventilation Device" Seventy-second Annual Session of the American Academy of Ophthalmology and Otolaryngology, Oct. 29-Nov. 3, 1967, Chicago, IL, 1 page.
Schmidt et al. "Transtympanic Aeration of the Middle Ear With Blocked Eustachian Tube" Acta Otolaryng., pp. 277-282 (1965).
Sheehy, "Collar Button Tube for Chronic Serous Otitis" Sixty-eighth Annual Session of the American Academy of Ophthalmology and Otolaryngology, Oct. 20-25, 1963, New York, NY, pp. 888-889.
Santa Barbara Medco, Inc. "Otological Ventilation Tubes" Product Brochure from http://www.sbmedco.com/ptfe_shepard.asp, 8 pages (Feb. 11, 2001).
Office Action for U.S. Appl. No. 14/457,293, dated Apr. 26, 2017, 11 pages.
Office Action for Chinese Application No. 201580050156.3, dated Nov. 28, 2018, 18 pages.

\* cited by examiner

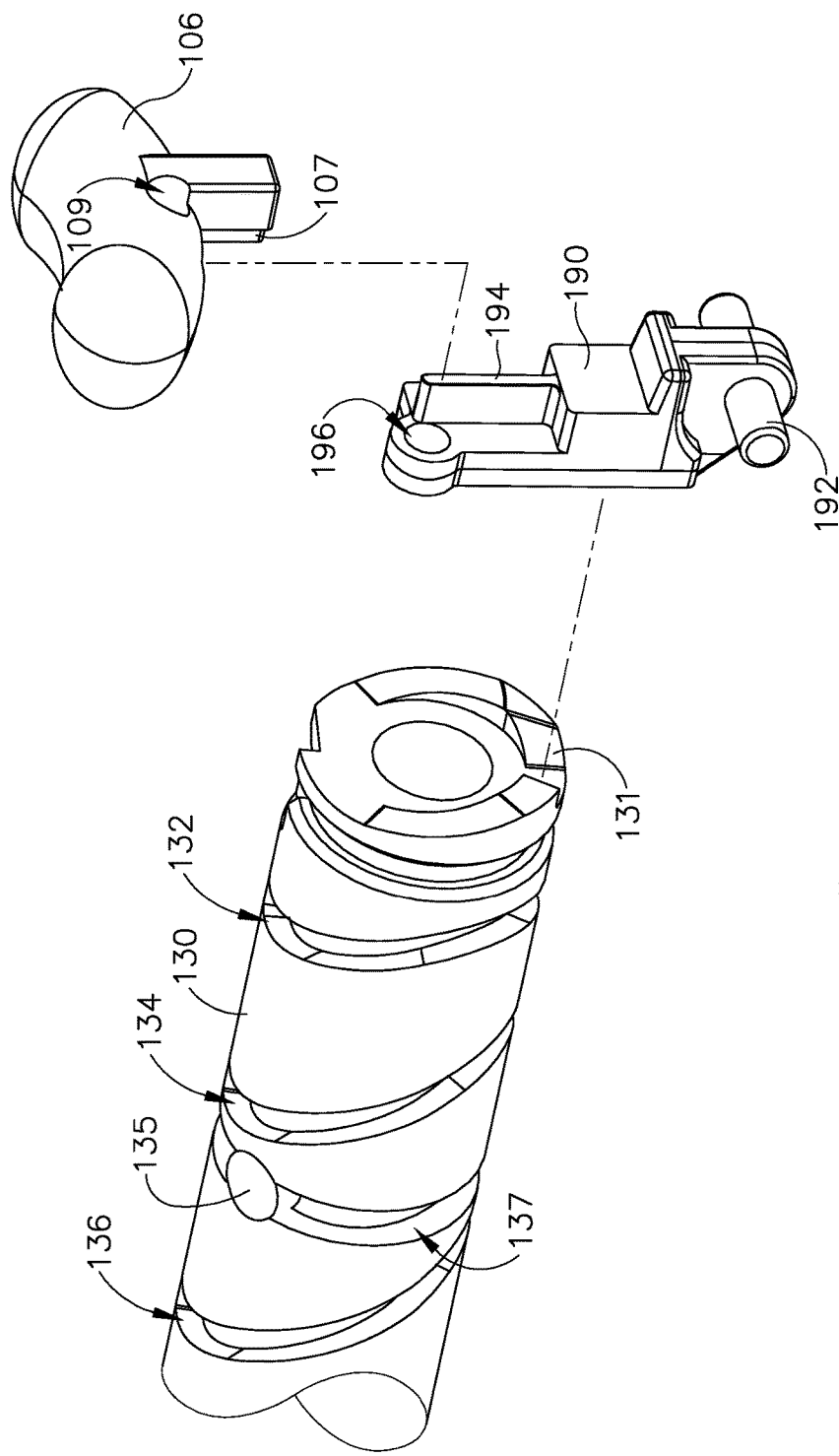

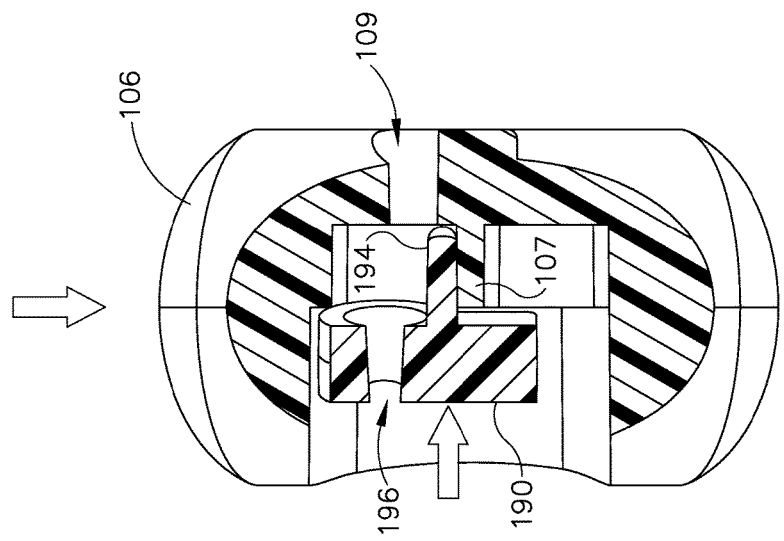
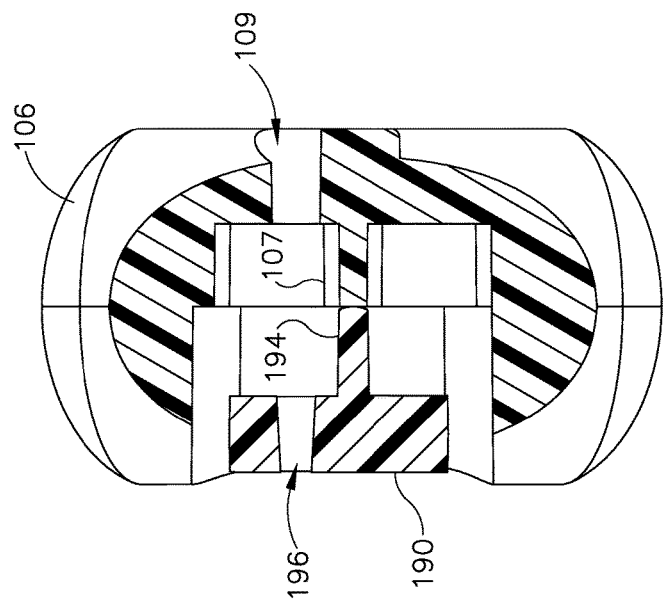
Fig. 16A
Fig. 16B

TYMPANOSTOMY TUBE DELIVERY DEVICE WITH ROTATABLE

BACKGROUND

Some children may exhibit recurrent episodes of otitis media and/or otitis media with effusion. Treatment of severe cases may involve the placement of a pressure equalization tube or tympanostomy tube through the tympanic membrane to provide adequate drainage of the middle ear by providing fluid communication between the middle and outer ear. In particular, such a tube may provide a vent path that promotes drainage of fluid from the middle ear via the Eustachian tube and may thus reduce stress imposed on the tympanic membrane from pressure within the middle ear. This may further reduce the likelihood of future infections and pressure induced ruptures of the tympanic membrane. Pressure equalization tubes may fall out spontaneously within about a year of placement. Exemplary pressure equalization tube delivery systems are disclosed in U.S. Pat. No. 8,052,693, entitled "System and Method for the Simultaneous Automated Bilateral Delivery of Pressure Equalization Tubes," issued Nov. 8, 2011, the disclosure of which is incorporated by reference herein. Additional exemplary pressure equalization tube delivery systems are disclosed in U.S. Pat. No. 8,249,700, entitled "System and Method for the Simultaneous Bilateral Integrated Tympanic Drug Delivery and Guided Treatment of Target Tissues within the Ears," issued Aug. 21, 2012, the disclosure of which is incorporated by reference herein. Still additional exemplary pressure equalization tube delivery systems are disclosed in U.S. Pub. No. 2011/0015645, entitled "Tympanic Membrane Pressure Equalization Tube Delivery System," published Jan. 20, 2011, the disclosure of which is incorporated by reference herein.

Insertion of a pressure equalization tube may be performed using general anesthesia in some cases, which may require additional resources such as an operating room, the presence of an anesthesiologist, and time in a recovery room. Furthermore, the use of general anesthesia may include certain risks that a patient may or may not be comfortable with undertaking. Some pressure equalization tube delivery systems and methods provide a local anesthetic through iontophoresis. Examples of such systems and methods are disclosed in U.S. Pub. No. 2010/0198135, entitled "Systems and Methods for Anesthetizing Ear Tissue," published Aug. 5, 2010, the disclosure of which is incorporated by reference herein. Additional examples of such systems and methods are disclosed in U.S. Pat. No. 8,192,420, entitled "Iontophoresis Methods," issued Jun. 5, 2012, the disclosure of which is incorporated by reference herein.

While a variety of pressure equalization tube delivery systems and methods have been made and used, it is believed that no one prior to the inventor(s) has made or used an invention as described herein.

BRIEF DESCRIPTION OF THE DRAWINGS

It is believed the present invention will be better understood from the following description of certain examples taken in conjunction with the accompanying drawings, in which like reference numerals identify the same elements and in which:

FIG. 10 depicts an exploded perspective view of a trigger mechanism of the actuation features of FIG. 3;

FIG. 16A depicts a cross-sectional view of the pawl and button actuator of FIGS. 11 and 13, taken along line 16-16 of FIG. 15A, showing the button actuator arresting the pawl;

FIG. 16B depicts a cross-sectional view of the pawl and button actuator of FIGS. 11 and 13, taken along line 16-16 of FIG. 15A, showing the button actuator translated laterally to enable movement of the pawl;

Figure 1:
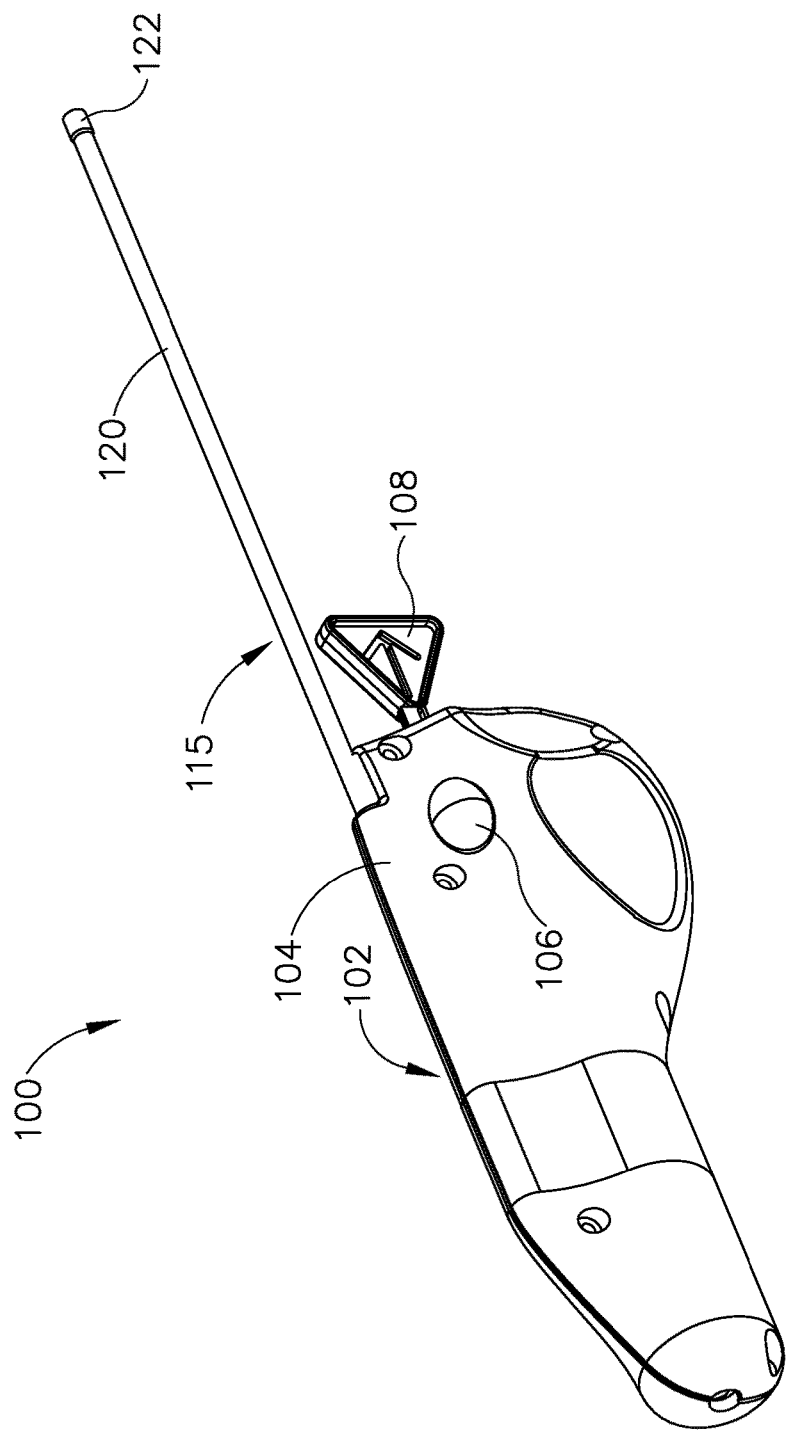
FIG. 1 depicts a perspective view of an exemplary pressure equalization tube delivery device (PETDD)

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Pressure Equalization Tube Delivery Instrument

As noted above, a pressure equalization (PE) tube may be delivered to the tympanic membrane (TM) of a patient as a way of treating, for example, otitis media. In some instances, a delivery instrument may be used to insert PE tubes in the tympanic membrane (TM) without the use of general anesthesia. FIG. 1 shows an exemplary pressure equalization tube delivery device (PETDD) (100) that may be used in such procedures. It should be understood that PETDD (100) may be used with an endoscope to provide visualization of the tympanic membrane (TM) during use of PETDD (100). It should also be understood that a patient may receive local anesthesia at the tympanic membrane (TM) through a process of iontophoresis before PETDD (100) is actuated to deploy a PE tube. By way of example only, such iontophoresis may be provided in accordance with at least some of the teachings of U.S. Pub. No. 2010/0198135, the disclosure of which is incorporated by reference herein; and/or in accordance with at least some of the teachings of U.S. Pat. No. 8,192,420, the disclosure of which is incorporated by reference herein. Other suitable ways in which PETDD (100) may be used will be apparent to those of ordinary skill in the art in view of the teachings herein.

As shown in FIG. 1, PETDD (100) of this example comprises a handpiece (102) and a shaft assembly (115) extending distally from handpiece (102). Hanpdiece (102) is formed by two housing (104) halves that are joined together and that include internal features configured to support various components of PETDD (100) as will be described below. Handpiece (102) is configured to be handheld, such that an operator may fully operate PETDD (100) using a single hand. A pushbutton (106) is slidably disposed in housing (104) and includes exposed portions extending laterally from each side of handpiece (102). Pushbutton (106) is operable to be pushed along a path that is transverse to handpiece (102) in order to actuate PETDD (100) as will be described in greater detail below. A pull-pin (108) extends distally from handpiece (102) and is configured to prevent pushbutton (106) from being actuated, thereby preventing PETDD (100) from being actuated, so long as pull-pin (108) is disposed in handpiece (102). Pull-pin (108) is nevertheless removable from handpiece (102) to effectively unlock pushbutton (106) and thereby enable actuation of PETDD (100). Shaft assembly (115) of the present example includes a cannula (120) comprising an elongate tube having a clear tip member (122) at the distal end of cannula (120). Clear tip member (122) is configured to contact a patient's tympanic membrane (TM) while enabling visualization of the distal end of cannula (120). In some versions, tip member (122) is formed of a soft or elastomeric material such as rubber, soft plastic, etc. This may dampen vibrations that might otherwise be transmitted from cannula (120) to the patient's tympanic membrane (TM) during firing of PETDD (100). In addition or in the alternative, tip member (122) may include some other kind of dampening feature as will be apparent to those of ordinary skill in the art in view of the teachings herein.

Figure 2:
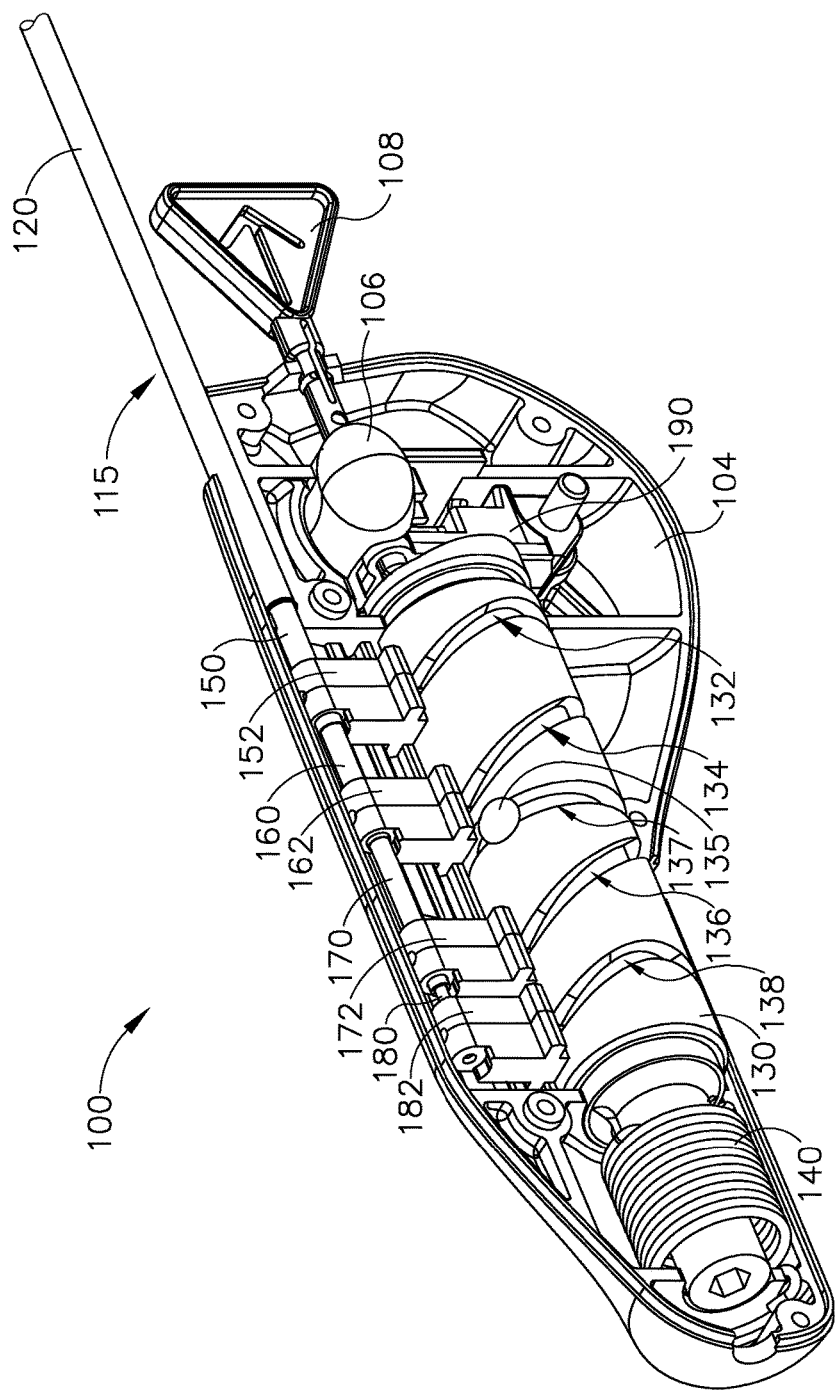
FIG. 2 depicts a perspective view of the PETDD of FIG. 1, with a housing half omitted.

As can be seen in FIG. 2, housing (104) supports a camshaft (130) and various other components. Camshaft (130) includes a dilator track (132), a shield tube track (134), a stopper track (137), a pusher track (136), and a piercer track (138). Tracks (132, 134, 136, 137, 138) are formed as recesses in camshaft (130) and each track (132, 134, 136, 137, 138) has a unique configuration in order to provide a particular sequence of operation of translating components as will be described in greater detail below. A torsion spring (140) is coupled to the proximal end of camshaft (130). Torsion spring (140) is also grounded against housing (104). Torsion spring (140) resiliently provides a rotational bias to camshaft (130). In particular, torsion spring (140) urges camshaft (130) to rotate in the clockwise direction (viewed from the distal end of PETDD (100) toward the proximal end of PETDD (100)) about the longitudinal axis of camshaft (130). As will be described in greater detail below (200), a trigger mechanism selectively resists such rotation. While torsion spring (140) is used to bias camshaft (130) in the present example, it should be understood that any other suitable types of components may be used to bias camshaft (130).

Figure 3:
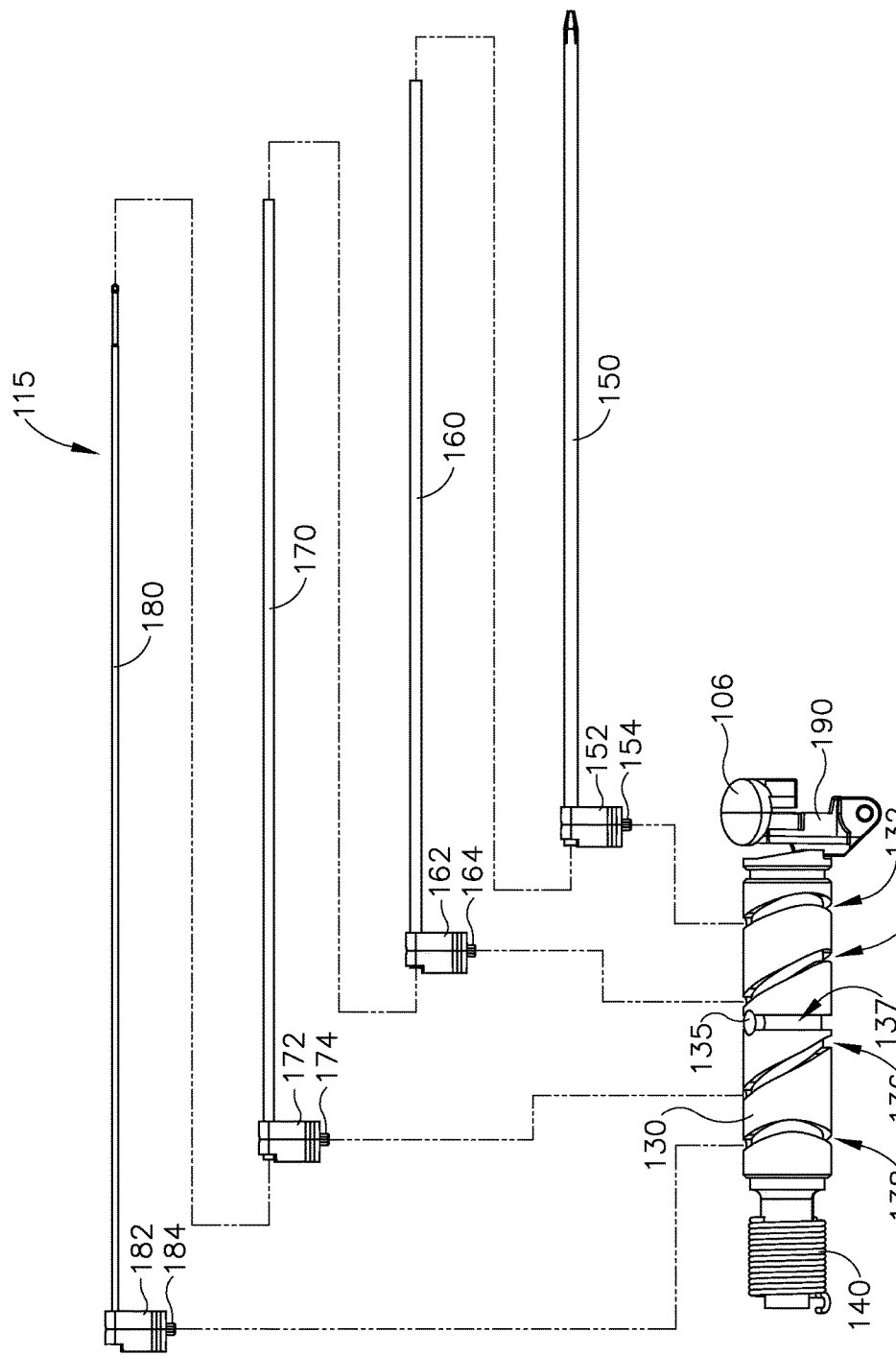
FIG. 3 depicts an exploded elevational view of actuation features of the PETDD of FIG. 1.

As shown in FIG. 3, various components are engaged with camshaft (130) and are thereby actuated by rotation of camshaft (130). In particular, a dilator tube (150), a shield tube (160), a pusher tube (170), and a piercer (180) are all engaged with camshaft (130). Tubes (150, 160, 170) and piercer (180) are all coaxially disposed within cannula (120) of shaft assembly (115). Piercer (180) is coaxially and slidably disposed within pusher tube (170), which is coaxially and slidably disposed within shield tube (160), which is coaxially and slidably disposed within dilator tube (150), which is coaxially and slidably disposed within cannula (120). Tubes (150, 160, 170) and piercer (180) all translate relative to cannula (120) in a particular sequence in order to deploy a PE tube as will be described in greater detail below. This sequence is driven by rotation of camshaft (130).

A cam follower (152) is fixedly secured to the proximal end of dilator tube (150). Cam follower (152) includes a laterally projecting pin (154) that is disposed in dilator track (132), such that rotation of camshaft (130) causes cam follower (152) and dilator tube (150) to translate. Similarly, a cam follower (162) is fixedly secured to the proximal end of shield tube (160). Cam follower (162) includes a laterally projecting pin (164) that is disposed in shield tube track (134), such that rotation of camshaft (130) causes cam follower (162) and shield tube (160) to translate. A cam follower (172) is fixedly secured to the proximal end of pusher tube (170). Cam follower (172) includes a laterally projecting pin (174) that is disposed in pusher tube track (136), such that rotation of camshaft (130) causes cam follower (172) and pusher tube (170) to translate. Finally, a cam follower (182) is fixedly secured to the proximal end of piercer (180). Cam follower (182) includes a laterally projecting pin (184) that is disposed in piercer track (138), such that rotation of camshaft (130) causes cam follower (182) and piercer (180) to translate. Stopper track (137) is simply annular in this example and includes a fixed elastomeric plug (135). An inwardly protruding boss (not shown) of housing (104) is disposed in stopper track (137). This boss remains disposed in stopper track (137) during rotation of camshaft (130).

Figure 4:
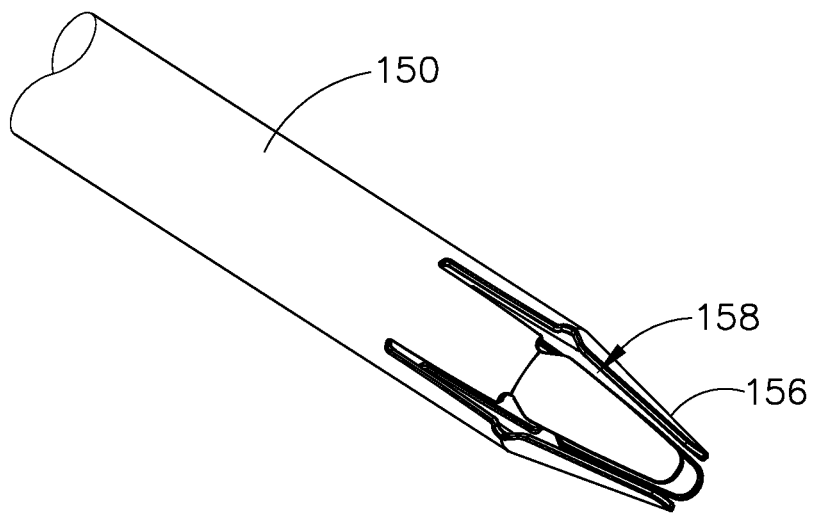
FIG. 4 depicts a perspective view of the distal end of a dilator of the actuation features of FIG. 3.
Figure 5:
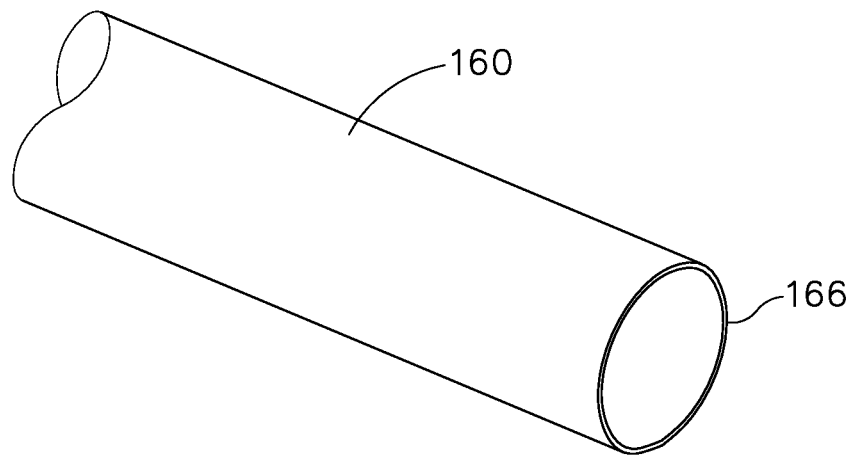
FIG. 5 depicts a perspective view of the distal end of a shield tube of the actuation features of FIG. 3.
Figure 6:
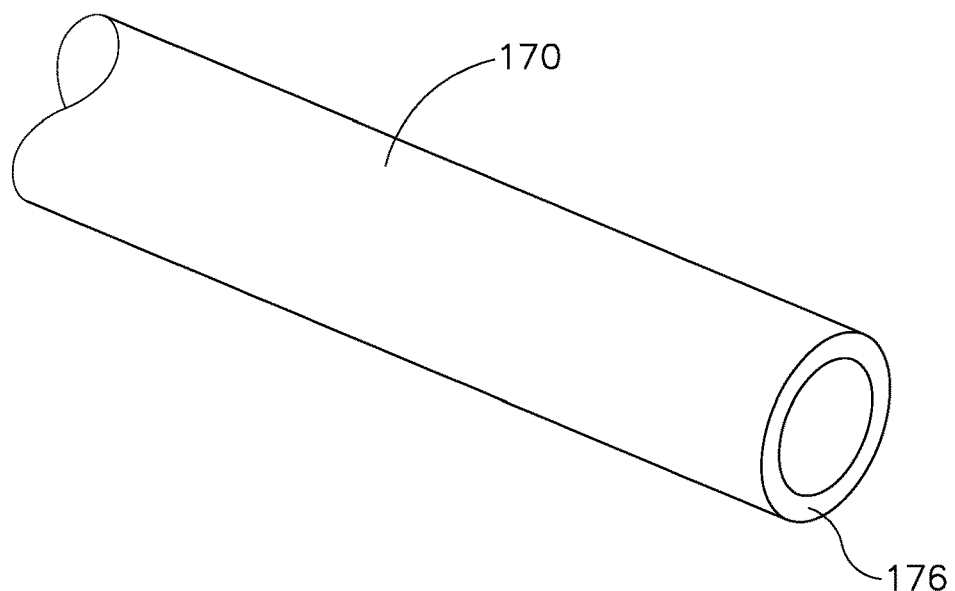
FIG. 6 depicts a perspective view of the distal end of a pusher of the actuation features of FIG. 3.
Figure 7:
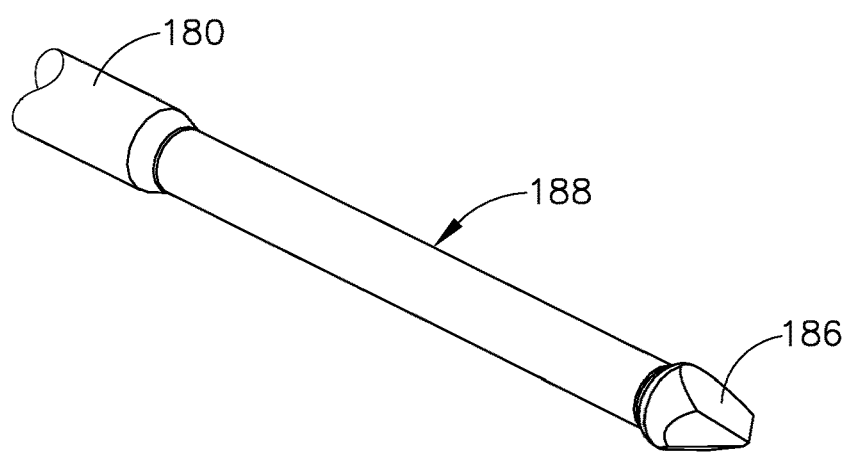
FIG. 7 depicts a perspective view of the distal end of a piercer of the actuation features of FIG. 3.

As shown in FIG. 4, the distal end of dilator tube (150) includes a plurality of generally flexible leaves (156) that are separated by longitudinally extending gaps (158). Leaves (156) are resiliently biased to assume the inwardly deflected positioning shown in FIG. 4; but are operable to flex outwardly from this positioning as will be described in greater detail below. As shown in FIG. 5, the distal end of shield tube (160) simply includes a circular edge (166). As shown in FIG. 6, the distal end of pusher tube (170) includes a distal face (176). In the present example, the difference between the inner diameter of pusher tube (170) and the outer diameter of pusher tube (170) is greater than the difference between the inner diameter of shield tube (160) and the outer diameter of shield tube (160). Thus, distal face (176) presents a more prominent contact surface than circular edge (166). As shown in FIG. 7, the distal end of piercer (180) includes a sharp, multi-faceted piercer tip (186) that is configured to pierce through a patient's tympanic membrane (TM). In the present example, piercer (180) also includes a neck-down region (188) having a reduced diameter.

Figure 8:
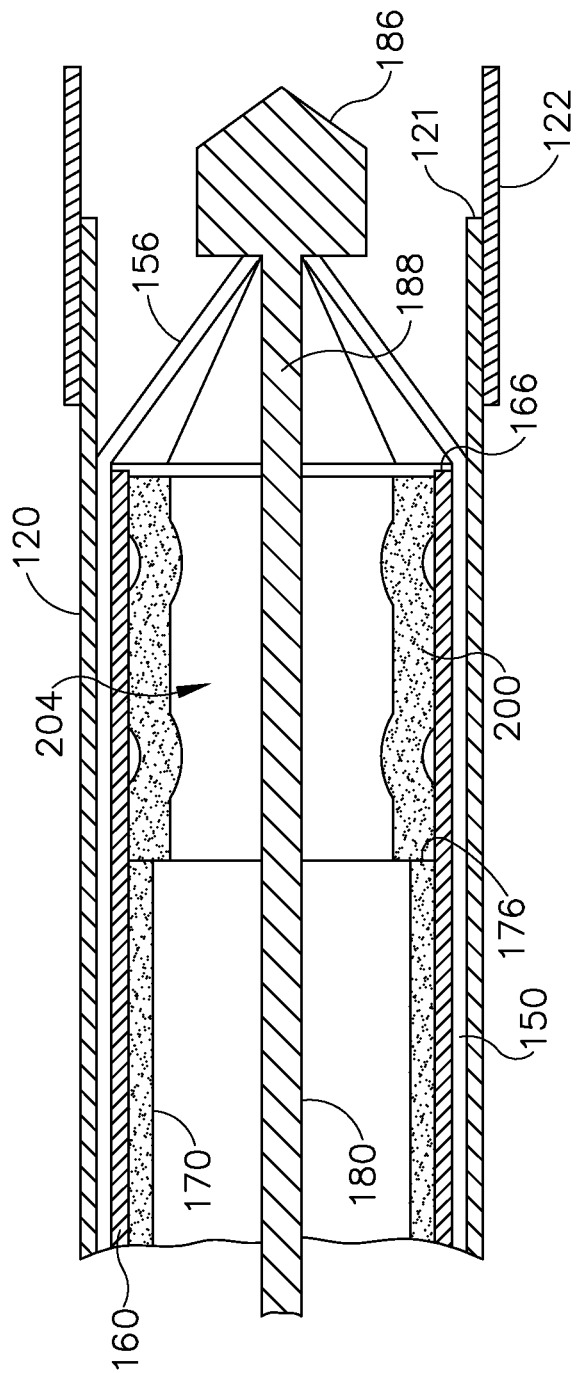
FIG. 8 depicts a cross-sectional side view of the actuation features of FIG. 3 with an exemplary pressure equalization (PE) tube.

FIG. 8 shows the positioning of tubes (150, 160, 170), piercer (180), and PE tube (200) within cannula (120) before camshaft (130) starts rotating from a home position. As shown, piercer tip (186) of piercer (180) is positioned distal to leaves (156) of dilator tube (150), such that leaves (156) are positioned about neck-down region (188) of piercer (180). PE tube (200) is positioned within the distal end of shield tube (160), whose distal edge (166) is just proximal to leaves (156). Pusher tube (170) is proximal to PE tube (200), with distal face (176) of pusher tube (170) abutting the proximal end of PE tube (200). In the present example, PE tube (200) is resiliently biased to assume a rivet-like shape presenting transverse petals (208) and a flange (206) (see FIG. 17-20). However, PE tube (200) is compressed against this bias, thereby assuming a generally cylindraceous configuration, when PE tube (200) is disposed within shield tube (160) as shown in FIG. 8.

Figure 9:
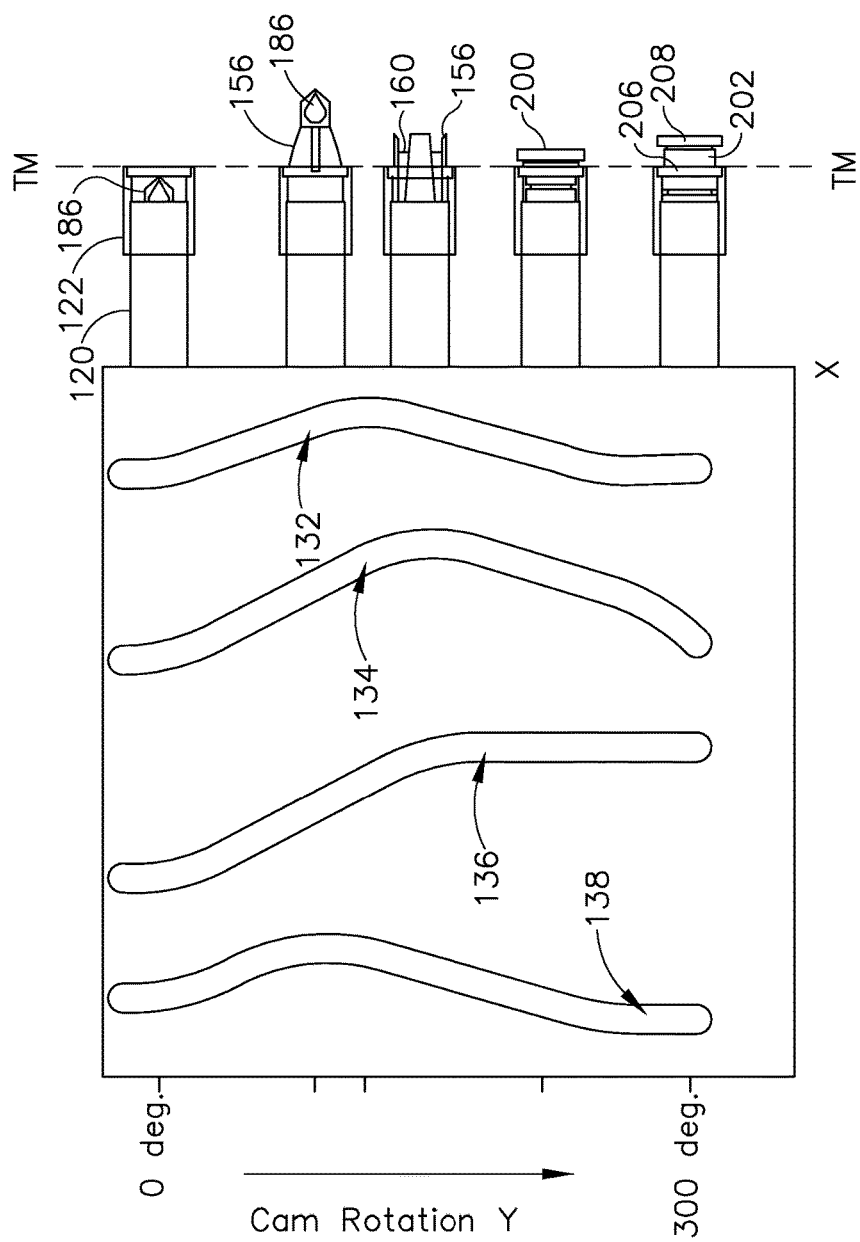
FIG. 9 depicts a displacement and operational diagram associated with the actuation features of FIG. 3.
Figure 12:
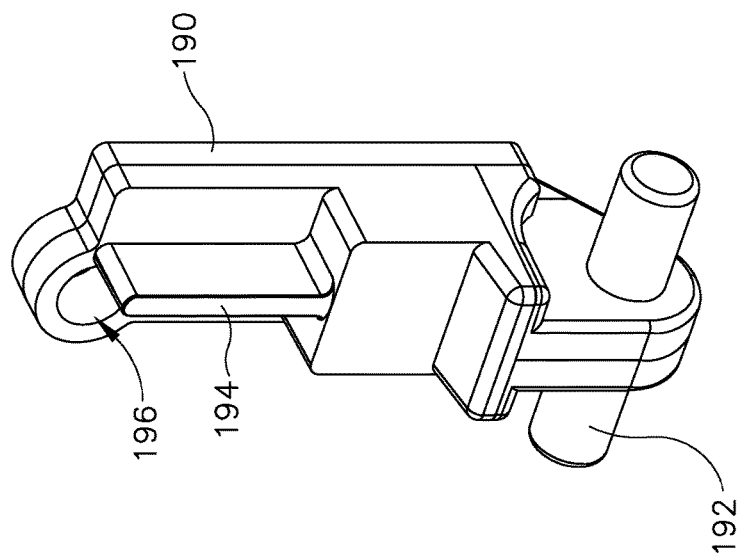
FIG. 12 depicts a perspective view of the distal side of the pawl of FIG. 11.
Figure 11:
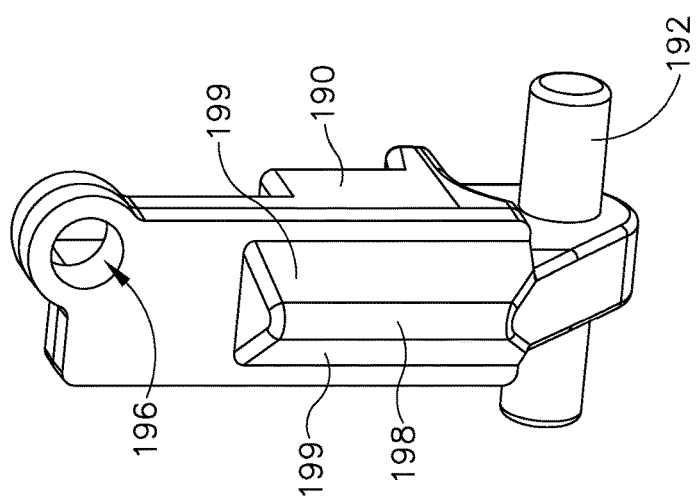
FIG. 11 depicts a perspective view of the proximal side of a pawl of the trigger mechanism of FIG. 10.

FIG. 9 depicts a sequence of operation that occurs upon rotation of camshaft (130) from a home position to an actuated position, where tracks (132, 134, 136, 138) are shown developed into a flat pattern for purpose of illustration. The sequence starts at the top region of FIG. 9, which shows the distal end of clear tip member (122) contacting the patient's tympanic membrane (TM). At this stage, tubes (150, 160, 170), piercer (180), and PE tube (200) are at the positions shown in FIG. 8. Once camshaft (130) starts rotating at the urging of torsion spring (140), pins (154, 164, 174, 184) begin to ride along their respective tracks (132, 134, 136, 138), such that piercer tip (186) and leaves (156) are driven distally through the patient's tympanic membrane (TM). While not directly shown in FIG. 8, it should be understood that tubes (160, 170) are also driven distally during this transition, though tubes (160, 170) remain proximal to clear tip member (122) at this stage. As camshaft (130) continues to rotate, piercer (180) begins retracting proximally while tubes (160, 170) continue to advance distally. As shown, shield tube (160) spreads leaves (156) outwardly from their default positions. This further dilates the puncture site in the tympanic membrane (TM). Shield tube (160) continues to contain PE tube (200) at this stage. As camshaft (130) continues to rotate, piercer (180) and dilator (150) retract proximally behind clear tip member (122). Shield tube (160) also begins to retract proximally, while pusher tube (170) remains longitudinally stationary. This relative movement uncovers the distal end of PE tube (200), such that the resilient bias of petals (208) causes petals (208) to flex to transverse positions, thereby effectively forming a flange on the far side of the tympanic membrane (TM). Piercer (180) eventually returns to the fully proximal position, dilator (170) eventually returns to the fully proximal position, and pusher tube (170) eventually reaches a fully distal position. As camshaft (130) continues to rotate, shield tube (160) continues to retract proximally while pusher tube (170) remains longitudinally stationary. This relative movement uncovers the proximal end of PE tube (200), such that the resilient bias of PE tube (200) is allowed to form flange (206) on the near side of the tympanic membrane (TM).

Camshaft (130) stops rotating when the inwardly protruding boss of housing (104) engages plug (135) in stopper track (137). The elastomeric nature of plug (135) provides a relatively soft stop, such that plug (135) acts as a damper. This may reduce jolting of PETDD (100) when camshaft (130) comes to a stop and/or may prevent camshaft (130) from making a popping or snapping sound when camshaft (130) comes to a stop. Upon completion of the above described sequence shown in FIG. 9, cannula (120) is withdrawn from the patient's ear, leaving the actuated PE tube (200) in place in the patient's tympanic membrane (TM). Petals (208) and flange (206) cooperate to maintain the position of PE tube (200) in TM, while the passageway (204) formed by the interior of PE tube (200) (see FIGS. 8 and 17-20) provides a path for fluid communication (e.g., venting) between the patient's middle ear and outer ear. This fluid path further provides pressure equalization between the patient's middle ear and outer ear and/or promotes drainage of fluid from the middle ear via the Eustachian tube.

Figure 14:
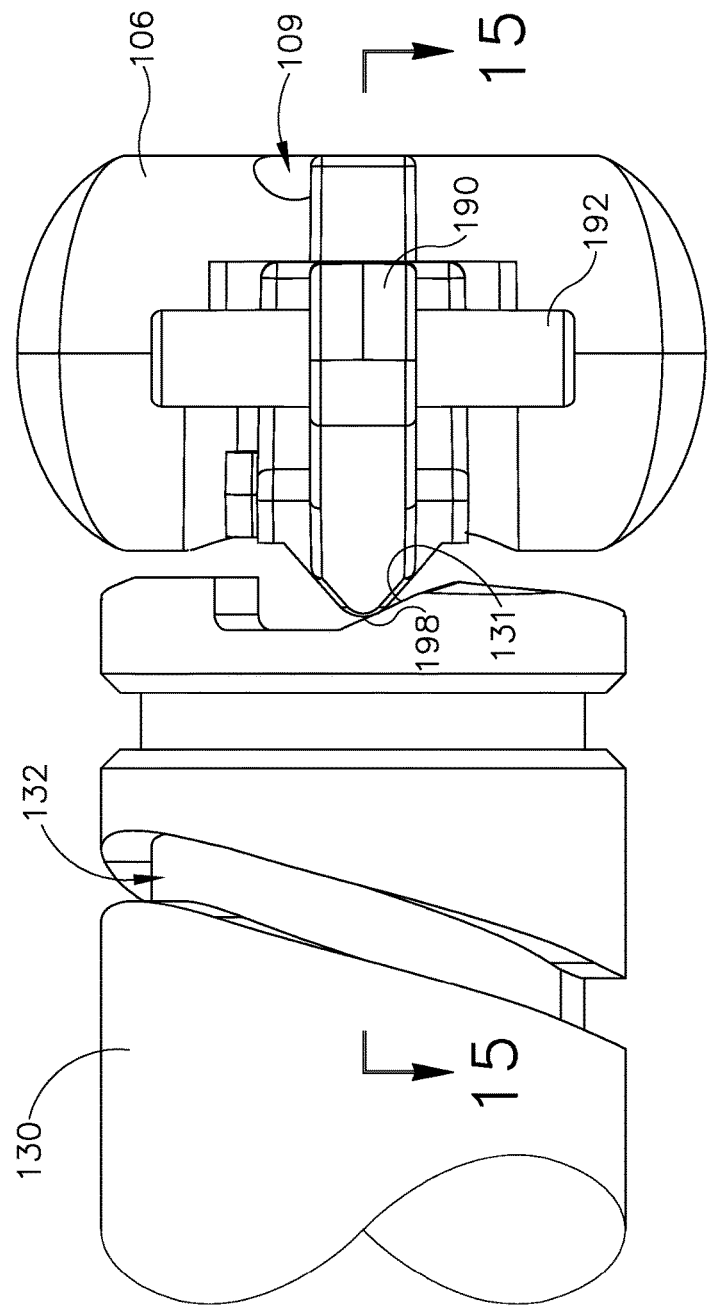
FIG. 14 depicts a bottom plan view of the trigger mechanism of FIG. 10, showing the pawl engaged with the camshaft.
Figure 15A:
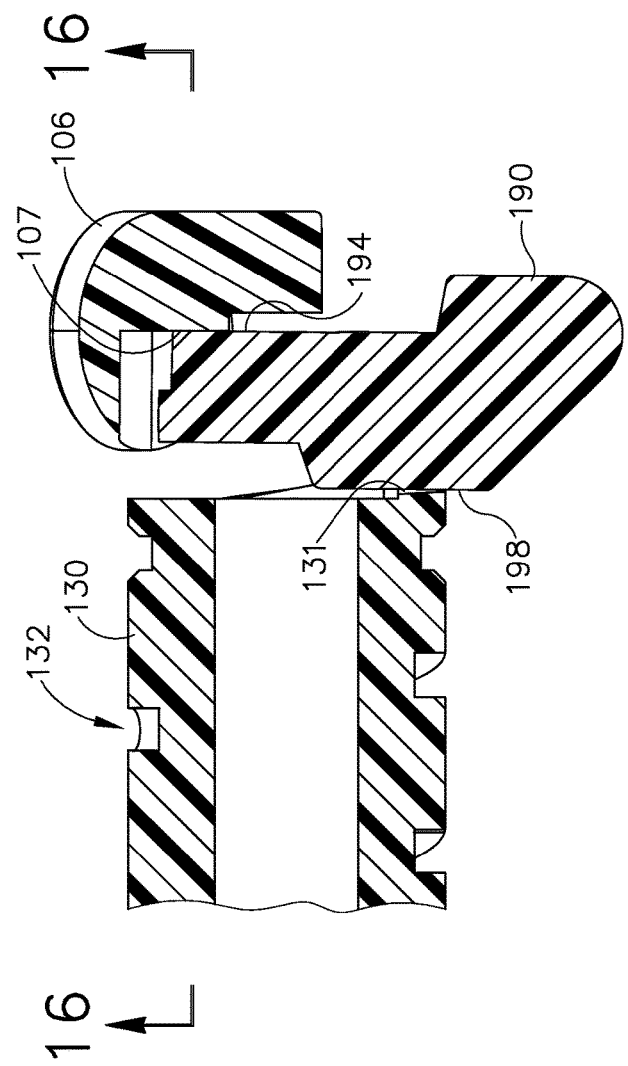
FIG. 15A depicts a cross-sectional view of the trigger mechanism of FIG. 10, taken along line 15-15 of FIG. 14, showing the pawl engaged with the camshaft.
Figure 15B:
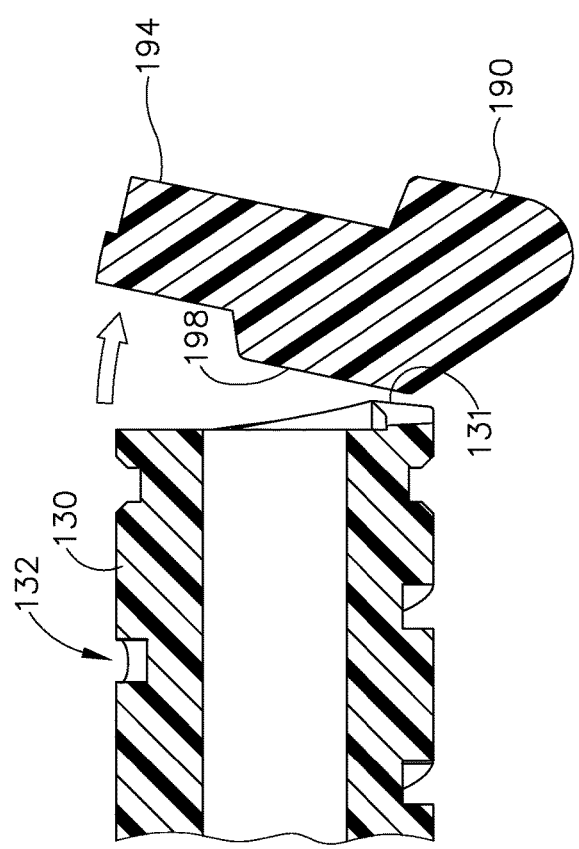
FIG. 15B depicts a cross-sectional view of the trigger mechanism of FIG. 10, taken along line 15-15 of FIG. 14, showing the pawl disengaged from the camshaft, with the button actuator omitted.
Figure 17:
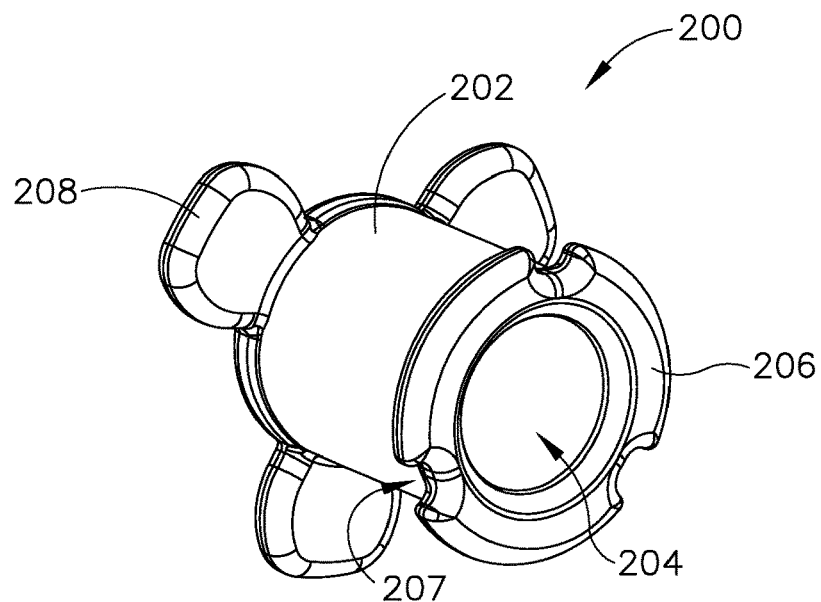
FIG. 17 depicts a perspective view of the proximal side of an exemplary PE tube suitable for delivery by the PETDD of FIG. 1.
Figure 18:
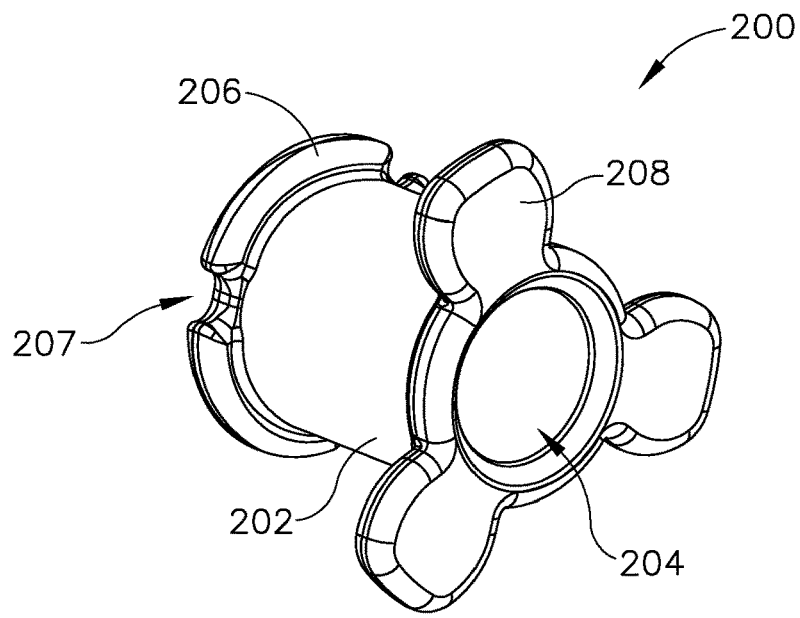
FIG. 18 depicts a perspective view of the distal side of the PE tube of FIG. 17.
Figure 19:
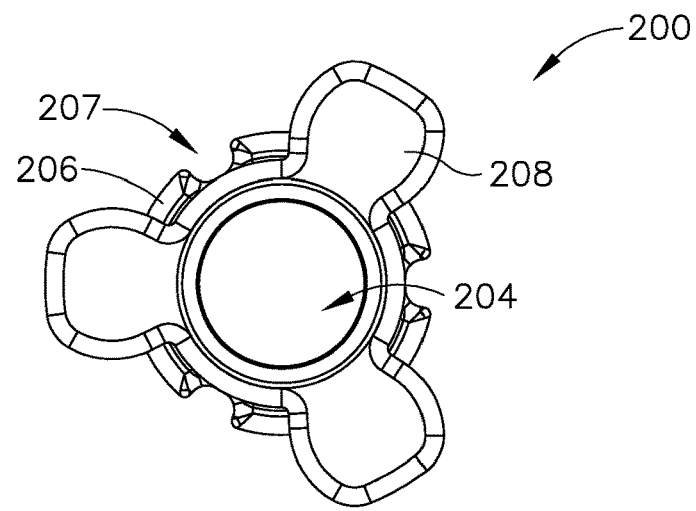
FIG. 19 depicts a distal elevational view of the PE tube of FIG. 17.
Figure 20:
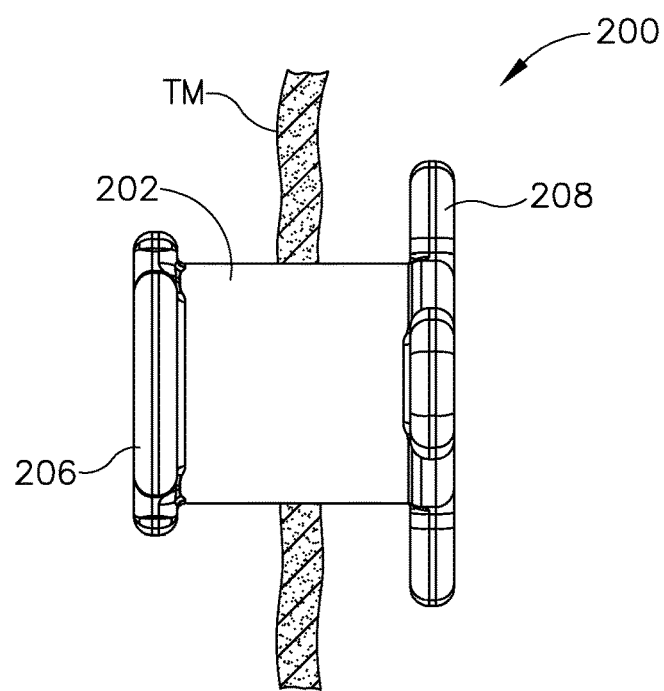
FIG. 20 depicts a side elevational view of the PE tube of FIG. 17, positioned within a tympanic membrane.

As noted above, PETDD (100) of the present example includes a trigger mechanism that is configured to selectively resist rotation of camshaft (130) by torsion spring (140). As best seen in FIGS. 10-16B, the trigger mechanism of this example comprises a pawl member (190) that selectively engages pushbutton (106) and camshaft (130). Pawl member (190) includes laterally extending pins (192) that couple pawl member (190) with housing (104). While housing (104) prevents pawl member (190) from moving laterally within housing (104), housing (104) permits pawl member (190) to pivot freely about pins (192) within housing (104). Pawl member (190) includes a distally facing boss rib (194) that extends vertically. Pawl member (190) also includes a pull-pin opening (196) and a proximally facing pawl ridge (198). Boss rib (194) is configured to selectively engage a proximally facing boss rib (107) of pushbutton (106) as will be described in greater detail below. Pull-pin opening (196) is configured to receive pull-pin (108), which assists to prevent pawl member (190) from pivoting about pins (192) when pull-pin (108) is disposed in pull-pin opening (196). Pawl ridge (198) includes chamfered lateral faces (199) and is configured to selectively engage a retention feature (131) of camshaft (130). In particular, when pawl member (190) is in a first position as shown in FIGS. 14, 15A, and 16A, pawl ridge (198) is engaged with retention feature (131) and prevents camshaft (130) from rotating despite the rotational bias provided by torsion spring (140). When pawl member (190) is pivoted to a second position as shown in FIGS. 15B and 16B, pawl ridge (198) disengages retention feature (131), enabling camshaft (130) to rotate under the influence of torsion spring (140) to provide the sequence of operation described above.

Figure 13:
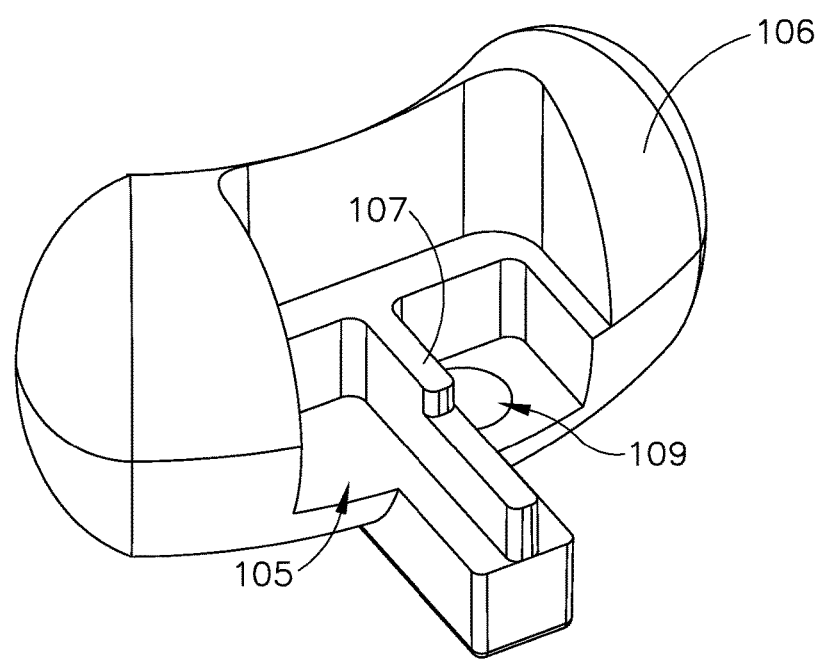
FIG. 13 depicts a perspective view of the proximal underside of a button actuator of the trigger mechanism of FIG. 10.

As best seen in FIGS. 10 and 13, pushbutton (106) includes a pull-pin opening (109) that is configured to receive pull-pin (108). Pushbutton (106) is prevented from translating laterally relative to housing (104) when pull-pin (108) is disposed within pull-pin opening (109). Pull-pin (108) thus provides a lockout for pushbutton (106). To unlock pushbutton (106), pull-pin (108) may be pulled distally out of housing (104). As noted above, pushbutton (106) also includes a proximally facing boss rib (107) that extends vertically. When pushbutton (106) is laterally centered within housing (104), boss rib (107) engages boss rib (194), as shown in FIGS. 15A and 16A. This engagement prevents pawl member (190) from pivoting distally about pins (192). Pushbutton (106) and pawl member (190) together thus effectively lock camshaft (130) when pushbutton (106) is laterally centered within housing (104).

When pushbutton (106) is laterally displaced relative to housing (104) (i.e., when a user depresses an exposed portion of pushbutton (106) laterally relative to housing (104)), bosses (107, 194) disengage such that pushbutton (106) no longer blocks pivoting of pawl member (190). Due to the torsional bias of camshaft (130), the ramped configuration of retention feature (131), and the chamfered lateral faces (199) of pawl ridge (198), camshaft (130) forces pawl member (190) to pivot out of the way to the position shown in FIGS. 15B and 16B when pushbutton (106) is no longer blocking pawl member (190). This enables camshaft (130) to complete the operational drive sequence described above. While pushsbutton (106) is depicted as being pushed in one lateral direction, it should be understood that the same triggering operation may be provided when pushbutton (106) is pushed in the opposite lateral direction from the center position. With portions of pushbutton (106) being exposed through housing (104) on each side of handpiece (102), this allows the operator to select which side of pushbutton (106) to press.

It should be understood that the foregoing components, features, and operabilities of PETDD (100) are merely illustrative examples. A PETDD (100) may include various other features in addition to or in lieu of those described above. By way of example only, any of the devices herein may also include one or more of the various features disclosed in any of the various references that are incorporated by reference herein. Some additional merely illustrative variations of PETDD (100) will be described in greater detail below, while other variations of PETDD (100) will be apparent to those of ordinary skill in the art in view of the teachings herein.

II. Exemplary Pressure Equalization Tube

FIGS. 17-20 show PE tube (200) in greater detail. PE tube (200) of this example includes a cylindraceous body (202) that defines a passageway (204). A flange (206) is located at the proximal end of body (202) while a set of petals (208) are located at the distal end of body (202). Flange (206) includes a plurality of inwardly directed recesses (207). Recesses (207) are configured to facilitate flexing of flange (206) from an outwardly extended position to a generally cylindraceous position where the material forming flange (206) extends longitudinally. While three recesses (207) are shown, it should be understood that any other suitable number of recesses (207) may be provided. Similarly, while three petals (208) are shown, it should be understood that any other suitable number of petals (208) may be provided.

PE tube (200) is formed of a resilient material that is biased to assume the rivet like configuration shown in FIGS. 17-20. However, flange (206) and petals (208) may be flexed inwardly toward the longitudinal axis of body (202) to provide PE tube (200) with a cylindraceous configuration. In particular, flange (206) and petals (208) may be flexed such that their outer surfaces are at the same radial distance from the longitudinal axis as the outer perimeter of body (202). This radial distance may be slightly less than the radial distance associated with the inner diameter of shield tube (160), such that PE tube (200) may collapse to fit within shield tube (160). When PE tube (200) is disposed in a tympanic membrane (TM), petals (208) are located medially (i.e., on the middle ear side) while flange (206) is located laterally (i.e., on the outer ear side). By way of example only, PE tube (200) may also be configured in accordance with at least some of the teachings of U.S. patent application Ser. No. 13/800,113, entitled "Tympanic Membrane Pressure Equalization Tube," filed on Mar. 13, 2013, published as U.S. Pub. No. 2014/0094733 on Apr. 3, 2014, the disclosure of which is incorporated by reference herein. Other suitable forms that PE tube (200) may take will be apparent to those of ordinary skill in the art in view of the teachings herein.

III. Exemplary Pressure Equalization Tube Delivery Instrument with Bendable and Rotatable Shaft Assembly Those of ordinary skill in the art will appreciate that the tympanic membrane (TM) may extend along a plane that is oblique to the direction of insertion of PETDD (100). In other words, the plane of the tympanic membrane (TM) may be obliquely angled relative to the longitudinal axis of shaft assembly (115). By way of example only, the tympanic membrane (TM) may define an angle between approximately 79 degrees and approximately 54 degrees with the longitudinal axis of shaft assembly (115). This oblique orientation of the tympanic membrane (TM) may pose difficulties with respect to some versions of a PETDD (100) that has a flat tip and/or a straight shaft assembly (115). For instance, inadequate apposition between the distal edge of tip member (122) and the tympanic membrane (TM) may lead to unsuccessful deployment of PE tube (200). This may prompt some operators of PETDD (100) to apply significant pressure against the tympanic membrane (TM), to deform the tympanic membrane (TM) into a position of substantial apposition with the flat-faced tip member (122) of PETDD (100). It may be desirable to maximize the apposition between the distal edge of tip member (122) and the tympanic membrane (TM), such as by enabling the distal edge of tip member (122) to complement the orientation of the tympanic membrane (TM) as much as possible, without requiring an operator to apply significant pressure against the tympanic membrane (TM) in order to achieve adequate apposition.

A rigid shaft assembly (115) may also adversely impact the ergonomics of PETDD (100) by forcing an operator to hold PETDD (100) at an uncomfortable angle to achieve a desired angle between shaft assembly (115) and the tympanic membrane (TM). Incorporating flexible and/or rotatable features into shaft assembly (115) may thus enhance the ergonomics of PETDD (100). In particular, a flexible and/or rotatable shaft assembly (115) may enable an operator to hold PETDD (100) at a more comfortable angle while still maintaining proper orientation of shaft assembly (115) relative to the patient's tympanic membrane (TM). Additionally, such features may facilitate positioning of an endoscope and/or other instrument with shaft assembly (115) in the patient's ear canal, thus promoting visualization of the tympanic membrane (TM). The following examples include merely illustrative variations of PETDD (100) that may provide flexibility and/or rotatability in shaft assembly (115).

Figure 21:
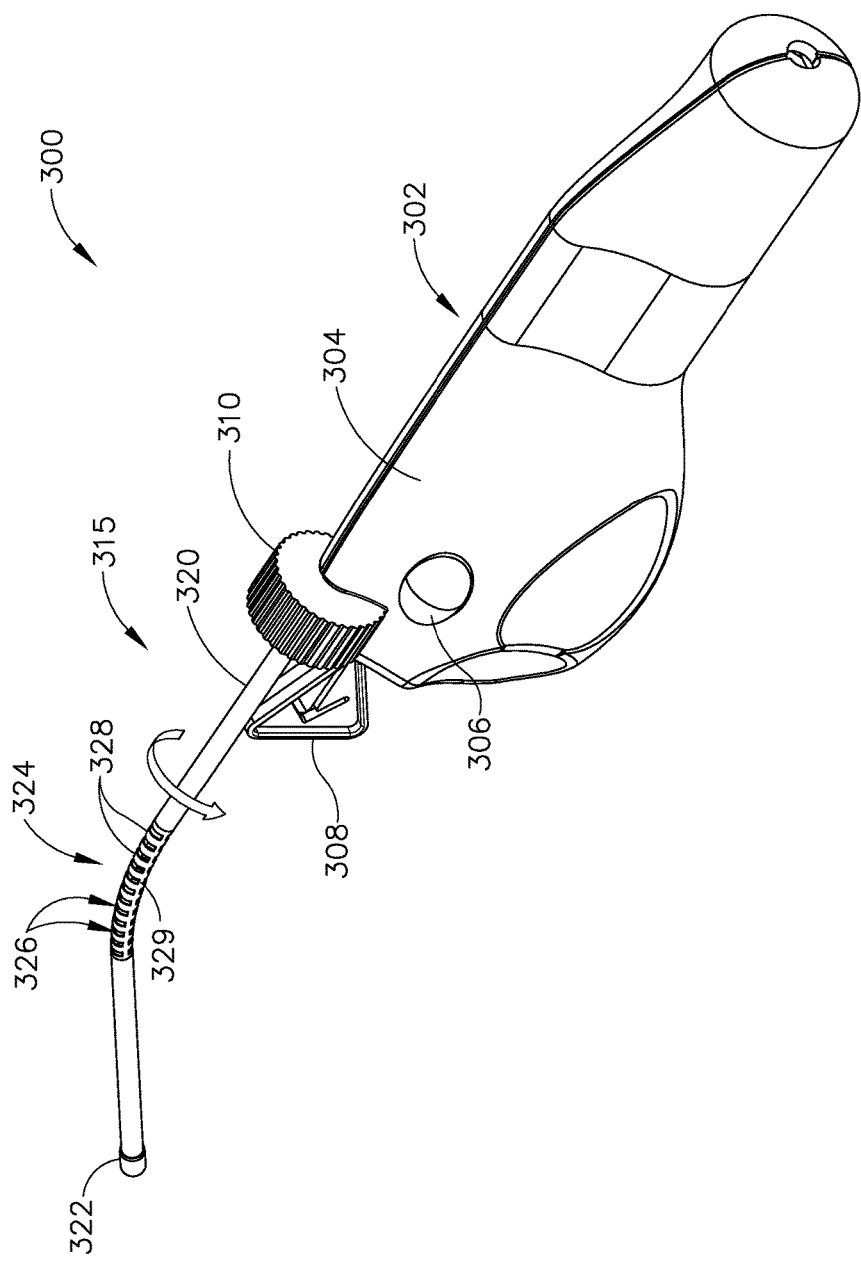
FIG. 21 depicts a perspective view of an exemplary alternative PETDD having a bendable and rotatable shaft assembly.

FIG. 21 depicts an exemplary alternative PETDD (300) having a bendable shaft assembly (315). All of the other components in this variation may be the same as those described above for PETDD (100), unless otherwise noted herein. As can be seen, PETDD (300) of this example comprises a handpiece (302) and a shaft assembly (315) extending distally from handpiece (302). Hanpdiece (302) is formed by two housing (304) halves that are joined together and that include internal features configured to support various components of PETDD (300) similarly as described above with respect to handpiece (102) of PETDD (100). Handpiece (302) is configured to be handheld, such that an operator may fully operate PETDD (300) using a single hand. A pushbutton (306) is slidably disposed in housing (304) and includes exposed portions extending laterally from each side of handpiece (302). Pushbutton (306) is operable to be pushed along a path that is transverse to handpiece (302) in order to actuate PETDD (300) similarly as described above with respect to pushbutton (106) of PETDD (100). A pull-pin (308) extends distally from handpiece (302) and is configured to prevent pushbutton (306) from being actuated, thereby preventing PETDD (300) from being actuated, so long as pull-pin (308) is disposed in handpiece (302). Pull-pin (308) is nevertheless removable from handpiece (302) to effectively unlock pushbutton (306) and thereby enable actuation of PETDD (300).

Figure 22:
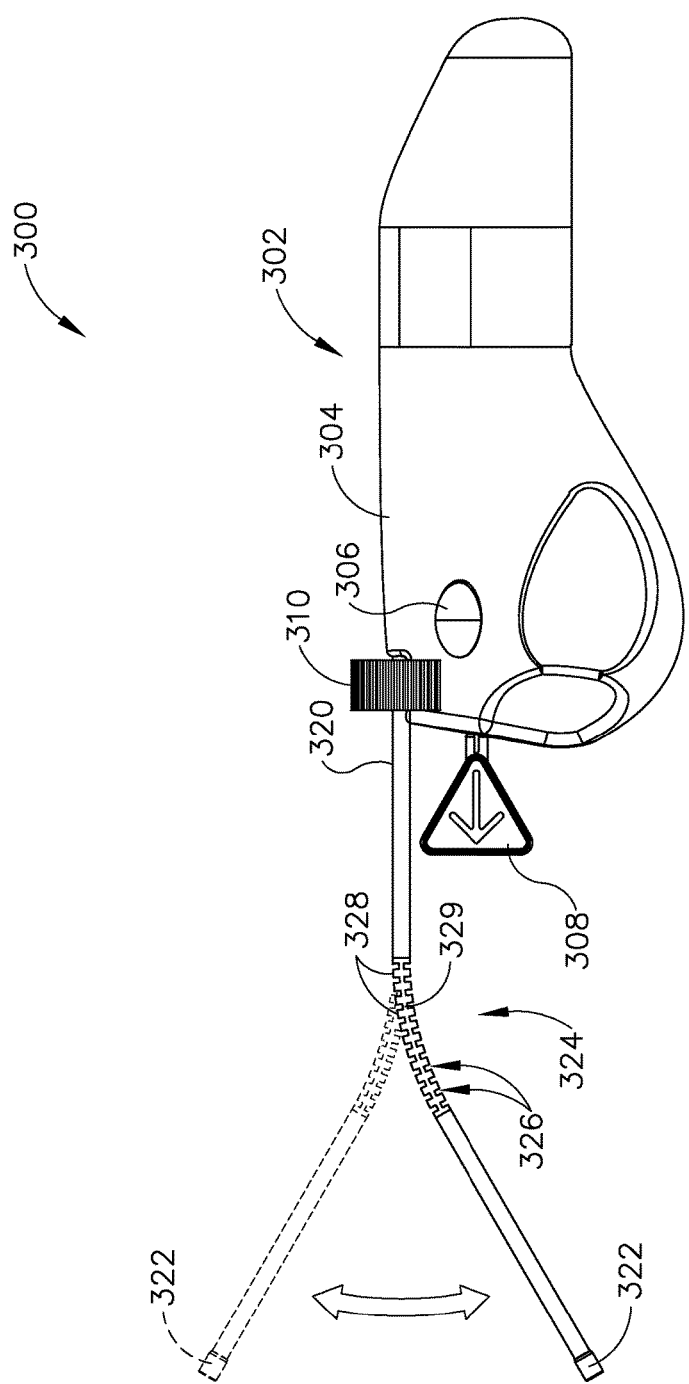
FIG. 22 depicts a side elevational view of the PETDD of FIG. 21 with an alternative position of the shaft assembly shown in phantom.

As can be seen in FIGS. 21 and 22, shaft assembly (315) of the present example includes a cannula (320) comprising an elongate tube having a bendable section (324), a thumbwheel (310), and a tip member (322) at the distal end of cannula (320). Thumbwheel (310) is fixedly secured to cannula (320) where cannula (320) and handpiece (302) meet. As will be described in greater detail below, thumbwheel (310) is operable to rotate cannula (320) about the longitudinal axis of cannula (320) relative to handpiece (302) when acted upon by a user. In the present example, handpiece (302) includes a bushing (312) which both supports cannula (320) in handpiece (302) and permits cannula (320) to rotate. In some versions, thumbwheel (310) may be fixedly secured to cannula (320) by adhesive bonding, over-molding, or any other means. Additionally, a proximal end of cannula (320) may include a flared end or other geometric features to aid with attachment. Yet in other examples, thumbwheel (310) may be integral to cannula (320) such that the two parts form a unitary part. Of course, thumbwheel (310) is entirely optional and may be eliminated in other versions.

Figure 24:
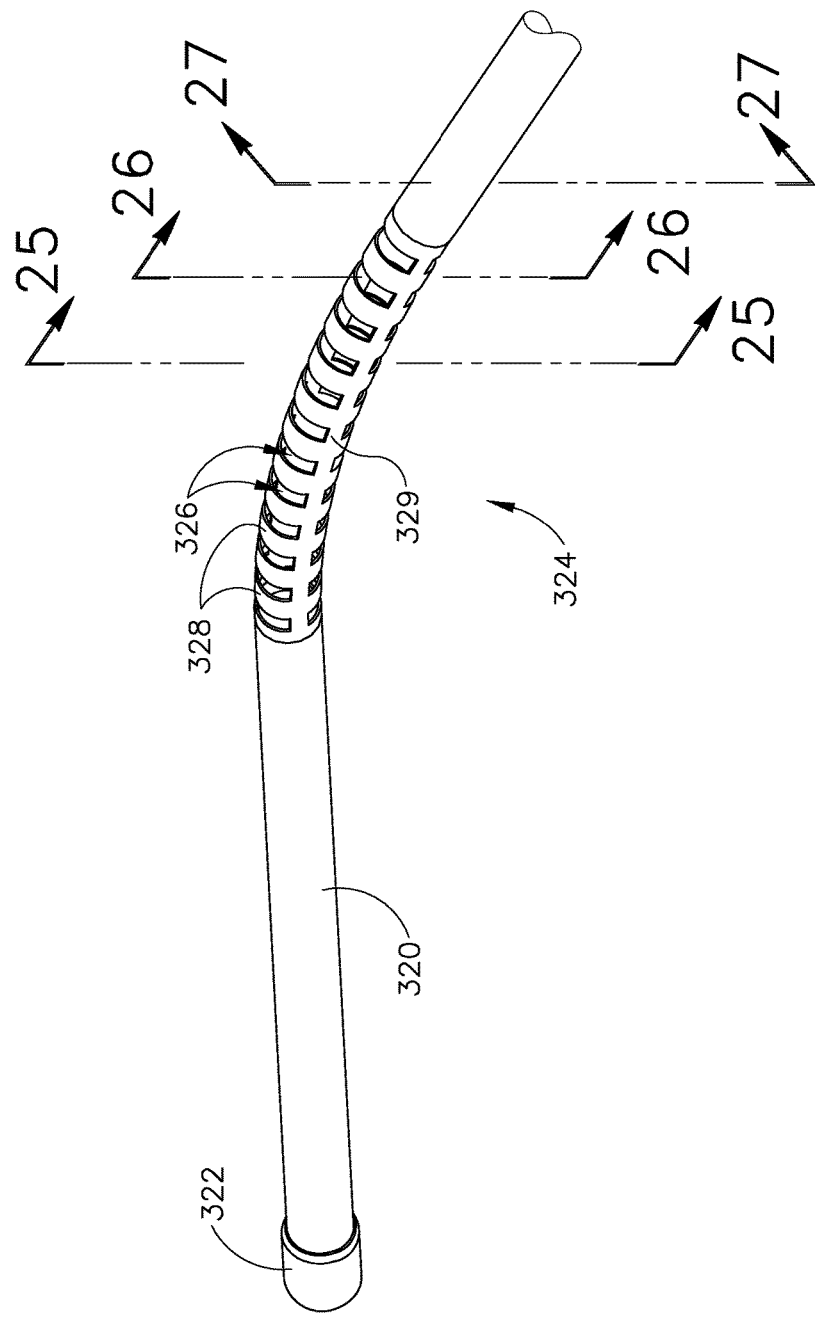
FIG. 24 depicts an enlarged perspective view of the shaft assembly of the PETDD of FIG. 21.
Figure 25:
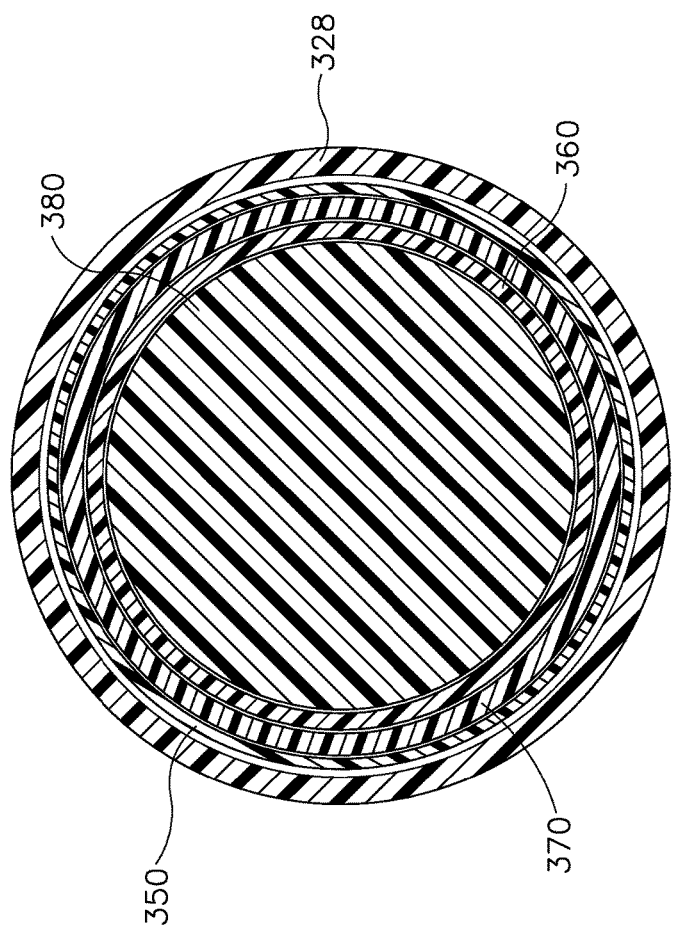
FIG. 25 depicts a cross-sectional front view of the shaft assembly of FIG. 24, with the cross-section taken along line 25-25 of FIG. 24.
Figure 26:
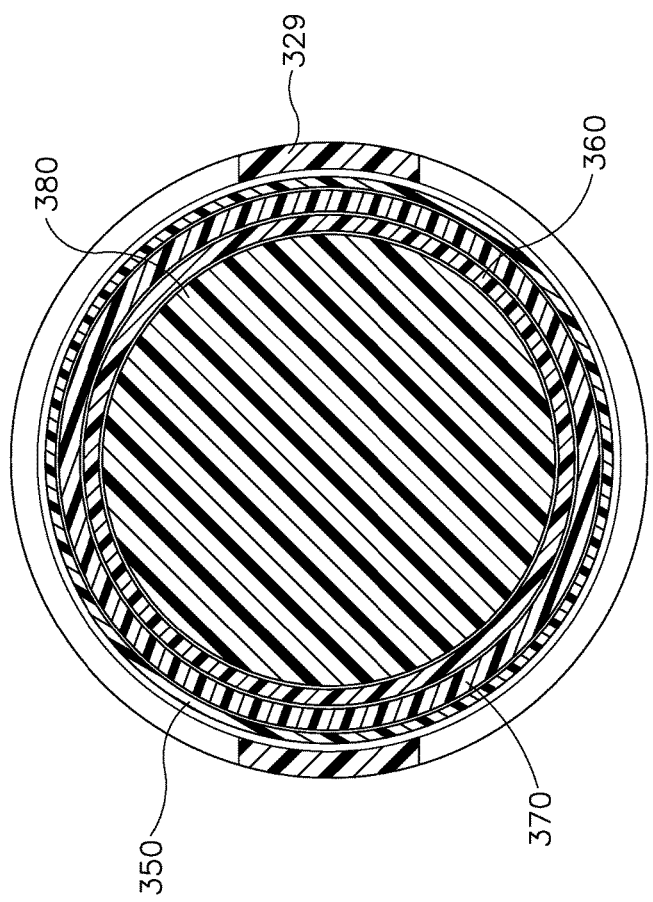
FIG. 26 depicts a cross-sectional front view of the shaft assembly of FIG. 24, with the cross-section taken along line 26-26 of FIG. 24.

As best seen in FIGS. 24-26, bendable section (324) comprises a plurality of cut outs (326), which define a plurality of ribs (328) on either side of cannula (320). Cut outs (326) only extend through a portion of cannula (320) such that a solid longitudinally extending member (329) of cannula (320) remains. Longitudinally extending member (329) maintains lateral stability of cannula (320), yet cut outs (326) and ribs (328) operate cooperatively to permit cannula (320) to bend along a plane as will be described in greater detail below. It should be understood that bendable section (324) as depicted shows merely one exemplary geometry suitable to permit cannula (320) to bend. In other examples, bendable section (324) could have any other suitable design such as a fluid linkage and/or other bendable structure as will be apparent to those of ordinary skill in the art in view of the teachings herein.

Tip member (322) is configured to contact a patient's tympanic membrane (TM). In some versions, tip member (322) may be integral to cannula (320) such that cannula (320) and tip member (322) are of a unitary part. In other versions tip, member (322) may be a separate component fixedly secured to the distal end of cannula (320). In either case, tip member (322) may be configured to be clear or opaque. Where clear, tip member (322) may enable enhanced visualization of a patient's tympanic membrane (TM). Although the distal end of tip member (322) is shown as being orthogonal relative to the longitudinal axis of cannula (320), it should be understood that other distal end geometries may be used. For instance, the distal end of tip member (322) may be obliquely angled relative to the longitudinal axis of cannula (320) to accommodate patients with obliquely angled TM's. Examples of such obliquely angled distal ends of tip member may be configured in accordance with at least some of the teachings of U.S. patent application Ser. No. 13/804,553, entitled "Features to Improve and Sense Tympanic Membrane Apposition by Tympanostomy Tube Delivery Instument," filed on Mar. 14, 2013, the disclosure of which is incorporated by reference herein. Of course, any other suitable configuration of tip member (322) may be used as will be apparent to those of ordinary skill in the art in view of the teachings herein.

Cannula (320) and/or tip member (322) may be formed of the same materials or different materials. For instance, in some versions cannula (320) and/or tip member (322) may be formed of a soft or elastomeric material such as rubber, soft plastic, nylon, polyether ether ketone (PEEK), etc. Yet in other versions cannula (320) and/or tip member (322) may be formed of a hard, more resilient material such as stainless steel, aluminum, or the like. In still other examples, cannula (320) could comprise a rigid material proximal to bendable section (324), a flexible material at bendable section (324), and a rigid material distal to bendable section (324). Alternatively, bendable section (324) could be formed of a malleable material. As yet another merely illustrative example, bendable section (324) may be formed of a plurality of short, rigid segments that are pivotally coupled together. When cannula (320) and/or tip member (322) is comprised of a soft or elastomeric material, such a material may dampen vibrations that might otherwise be transmitted from cannula (120) to the patient's tympanic membrane (TM) during firing of PETDD (300). In addition or in the alternative, tip member (322) may include some other kind of dampening feature as will be apparent to those of ordinary skill in the art in view of the teachings herein.

Figure 23:
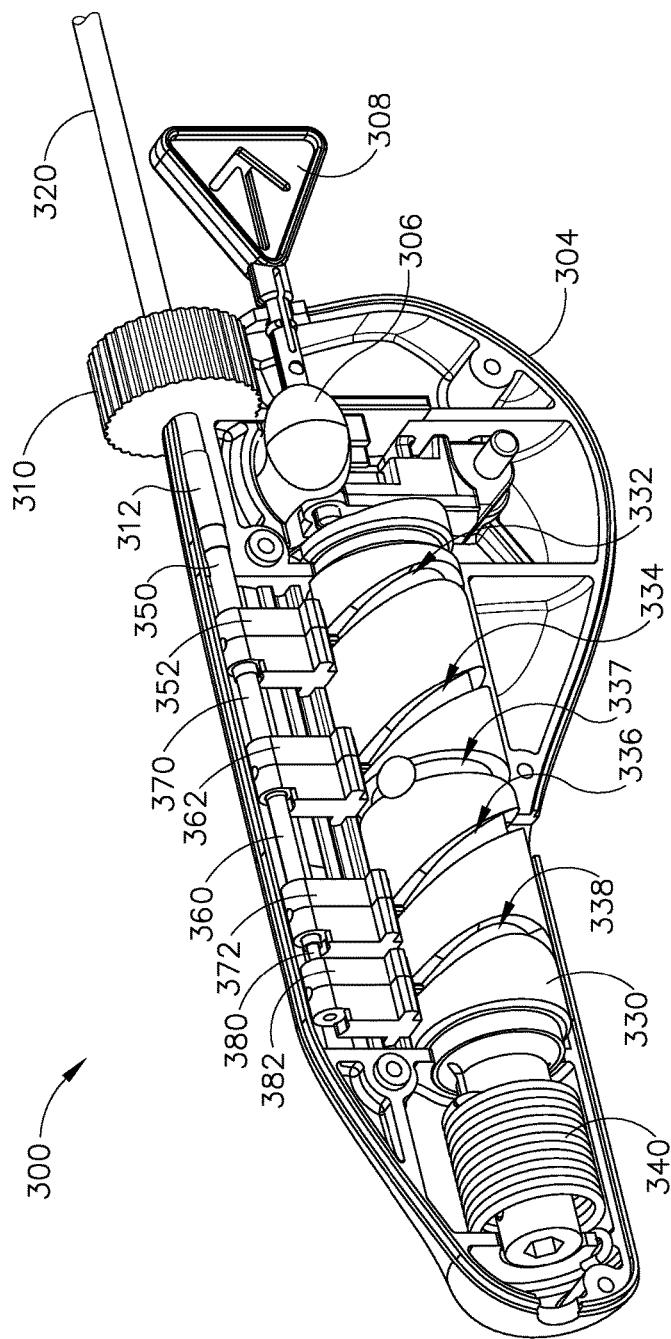
FIG. 23 depicts a perspective view of the PETDD of FIG. 21, with a housing half omitted.

As can be seen in FIG. 23, housing (304) supports a camshaft (330) and various other components. Camshaft (330) includes a dilator track (332), a shield tube track (334), a stopper track (337), a pusher track (336), and a piercer track (338). Tracks (332, 334, 336, 337, 338) are formed as recesses in camshaft (330) and each track (332, 334, 336, 337, 338) has a unique configuration in order to provide the same particular sequence of operation as similarly described above with respect to camshaft (130) of PETDD (100). A torsion spring (340) is coupled to the proximal end of camshaft (330). Torsion spring (340) is also grounded against housing (304). Torsion spring (340) resiliently provides a rotational bias to camshaft (330). In particular, torsion spring (340) urges camshaft (330) to rotate in the clockwise direction (viewed from the distal end of PETDD (300) toward the proximal end of PETDD (300)) about the longitudinal axis of camshaft (330). As was similarly described above with respect to PETDD (100), a trigger mechanism selectively resists such rotation. While torsion spring (340) is used to bias camshaft (330) in the present example, it should be understood that any other suitable types of components may be used to bias camshaft (330).

As similarly described above with respect to camshaft (130) of PETDD (100), various components are engaged with camshaft (330) and are thereby actuated by rotation of camshaft (330). In particular, a dilator tube (350), a shield tube (360), a pusher tube (370), and a piercer (380) are all engaged with camshaft (330). Tubes (350, 360, 370) and piercer (380) are all coaxially disposed within cannula (320) such that tubes (350, 360, 370) and piercer (380) together form shaft assembly (315). Piercer (380) is coaxially and slidably disposed within pusher tube (370), which is coaxially and slidably disposed within shield tube (360), which is coaxially and slidably disposed within dilator tube (350), which is coaxially and slidably disposed within cannula (320). Tubes (350, 360, 370) and piercer (380) all translate relative to cannula (320) in a particular sequence in order to deploy a PE tube as was similarly described above. This sequence is driven by rotation of camshaft (330).

A cam follower (352) is fixedly secured to the proximal end of dilator tube (350). Cam follower (352) includes a laterally projecting pin (not shown) that is disposed in dilator track (332), such that rotation of camshaft (330) causes cam follower (352) and dilator tube (350) to translate. Similarly, a cam follower (362) is fixedly secured to the proximal end of shield tube (360). Cam follower (362) includes a laterally projecting pin (not shown) that is disposed in shield tube track (334), such that rotation of camshaft (330) causes cam follower (362) and shield tube (360) to translate. A cam follower (372) is fixedly secured to the proximal end of pusher tube (370). Cam follower (372) includes a laterally projecting pin (not shown) that is disposed in pusher tube track (336), such that rotation of camshaft (330) causes cam follower (372) and pusher tube (370) to translate. Finally, a cam follower (382) is fixedly secured to the proximal end of piercer (380). Cam follower (382) includes a laterally projecting pin (not shown) that is disposed in piercer track (338), such that rotation of camshaft (330) causes cam follower (382) and piercer (380) to translate. Stopper track (337) is simply annular in this example and includes a fixed elastomeric plug (335). An inwardly protruding boss (not shown) of housing (304) is disposed in stopper track (337). This boss remains disposed in stopper track (337) during rotation of camshaft (330).

Although not shown, tubes (350, 360, 370) and piercer (380) have distal ends configured similarly to the distal ends of tubes (150, 160, 170) and piercer described above. For instance, dilator tube (350) includes a plurality of flexible leaves (not shown) that are resiliently biased inwardly. Likewise, the distal end of shield tube (360) and pusher tube (370) include a circular edge (not shown) and a distal face (not shown), respectively. Similar to distal face (176) discussed above, distal face of pusher tube comprises a more prominent contact surface relative to circular edge of shield tube (160). Additionally, piercer (180) includes a sharp multi-faceted piercer tip (not shown) that is configured to pierce through a patient's tympanic membrane (TM). Although tubes (350, 360, 370) and piercer (380) are described above as having distal ends that are similar to those of tubes (150, 160, 170) and piercer (180), no such limitation is intended. Indeed, tubes (350, 360, 370) and piercer (380) may comprise any suitable distal end configurations as will be apparent to those of ordinary skill in the art in view of the teachings herein.

In the present example, at least a portion of each tube (350, 360, 370) and piercer (380) is flexible. By way of example only, at least a portion of each tube (350, 360, 370) and piercer (380) may be formed of nylon, PEEK, some other flexible polymer, a flexible metal, and/or any other suitable flexible material(s) as will be apparent to those of ordinary skill in the art in view of the teachings herein. Such a flexible portion of each tube (350, 360, 370), and piercer (380) extends through bendable section (324) of cannula (320). In addition to allowing bendable section (324) to flex along a plane, the flexible region(s) of tubes (350, 360, 370) and piercer (380) enable tubes (350, 360, 370) and piercer (380) to translate longitudinally through bendable section (324) while bendable section (324) is in a bent state. In some versions, tubes (350, 360, 370) and piercer (380) each have a rigid distal end or rigid distal portion, in addition to having a flexible region located proximal to the rigid distal end or portion. By way of example only, the rigid distal end or rigid distal section of each tube (350, 360, 370) and piercer (380) may be formed of a rigid metal, a rigid polymer, and/or any other suitable rigid material(s) as will be apparent to those of ordinary skill in the art in view of the teachings herein. It should also be understood that a proximal section of each tube (350, 360, 370) and piercer (380) may be rigid, in addition to a distal portion or distal end of each tube (350, 360, 370) and piercer (380) being rigid, with the intermediate region of the length of each tube (350, 360, 370) and piercer (380) being flexible. Various suitable combinations of rigidity and flexibility in the construction of tubes (350, 360, 370) and piercer (380) will be apparent to those of ordinary skill in the art in view of the teachings herein.

Tubes (350, 360, 370) are configured to be used in conjunction with PE tube (200) as similarly described above with respect to PETDD (100). In particular, PE tube (200), tubes (350, 360, 370), and piercer (380) may all be sequentially actuated within cannula (320). The particular sequence is controlled by tracks (332, 334, 336, 338) as camshaft (330) rotates and is substantially similar to the sequence described above with respect to FIG. 9. Thus, even though cannula (320) is bendable, PETDD (300) is still operable to penetrate a patient's tympanic membrane (TM) and deploy PE tube (200) using substantially the same mechanisms as those described above with respect to PETDD (100). In other versions, PETDD (300) may be configured for use without PE tube (200). For instance, PETDD (300) may simply be used to puncture a patient's tympanic membrane (TM) for fluid collection or other similar procedures.

FIG. 22 shows that cannula (320) is bendable to a variety of angles. By way of example only, cannula (230) may bend to achieve angles from approximately 0 degrees to approximately 60 degrees; or from approximately 0 degrees to approximately 45 degrees. In some versions, cannula (320) may be configured to be malleable such that it may be bent to a specific angular location and remain at that specific location without a continuously applied force. Yet in other versions, cannula (320) may merely be flexible such that it may be sustained in a particular angular location only when a continuous force is applied. In either case, such properties may be achieved by, at least in part, the materials used for cannula (320), tubes (350, 360, 370), and/or piercer (380). For instance, to achieve malleable properties, cannula (320) may be comprised of malleable alloys such as stainless steel alloys, aluminum alloys, shape memory alloys, or the like. Additionally, such malleable properties may be achieved with other materials such as malleable plastics or polymers. Alternatively, to achieve properties that render cannula flexible, non-malleable alloys or plastics may be used. Further, materials may be varied between cannula (320), tubes (350, 360, 370), and piercer (380) to render cannula (320) malleable, semi-malleable, or flexible. Of course, cannula (320), tubes (350, 360, 370), and piercer (380) may be comprised of any suitable material to have any suitable properties as will be apparent to those of ordinary skill in the art in view of the teachings herein.

Figure 27:
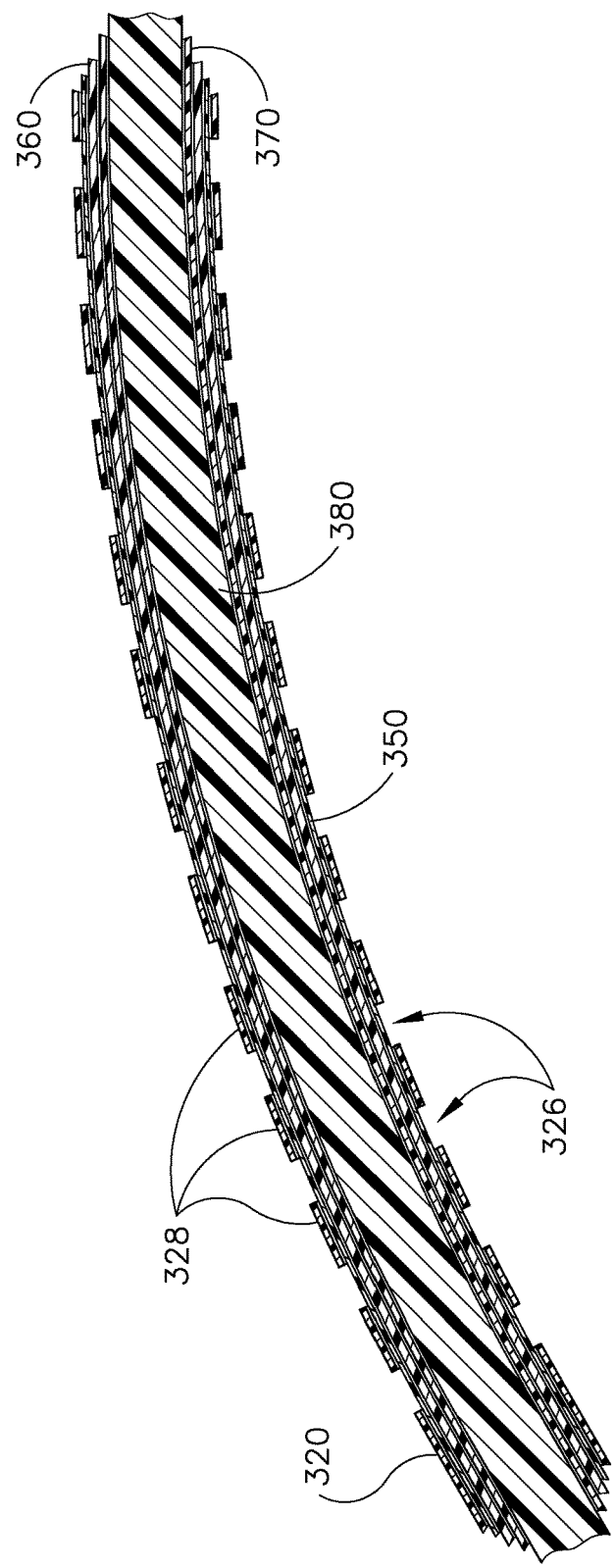
FIG. 27 depicts a cross-sectional side view of the shaft assembly of FIG. 24, with the cross-section taken along line 27-27 of FIG. 24.

As can be seen in FIGS. 25-27, tubes (350, 360, 370) and piercer (380) extend through bendable section (324) of cannula (320) and are configured to bend as cannula (320) bends. It should be understood that tubes (350, 360, 370) and piercer (380) are configured such that they may be sequentially actuated within cannula (320) even when cannula (320) is bent. In other words, cannula (320) tubes (350, 360, 370), and piercer (380) are configured to maintain a neutral axis throughout bendable section (324) such that each component maintains a consistent relationship with tip member (322) as cannula (320) is bent. In some versions, lubricant may be included between cannula (320), tubes (350, 360, 370), piercer (380) and cannula (320), although such lubricant is entirely optional.

Figure 28:
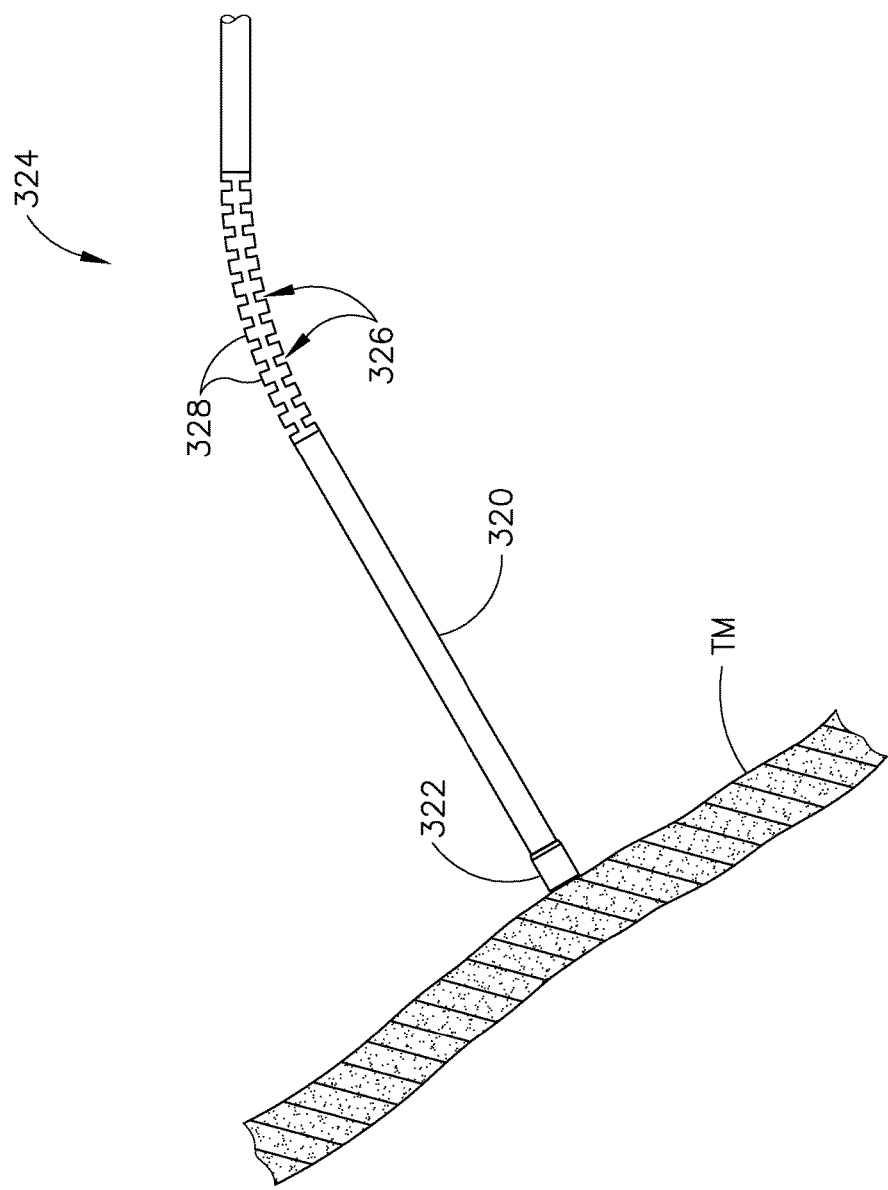
FIG. 28 depicts a side elevational view of the shaft assembly of FIG. 23 in contact with a tympanic membrane.

As noted above, cannula (320) is rotatable via thumbwheel (310). Thus, cannula (320) is operable to both bend and rotate relative to its longitudinal axis. In some versions, tubes (350, 360, 370) and piercer (380) may remain stationary while cannula (320) rotates. In some other versions, thumbwheel (310) may be configured to rotate all or some of tubes (350, 360, 370) and/or piercer (380) in conjunction with cannula (320). Still in other versions, tubes (350, 360, 370) and/or piercer tube (380) may be configured to be independently rotatable relative to cannula (320). For instance, piercer tube (380) may be independently rotatable to optimize piercing. Such a combination of bendability and roatatability may increase visualization of, and access to, the tympanic membrane (TM) of a patient. In an exemplary use of PETDD (300), cannula (320) may be pre-bent outside of a patient to account for an obliquely oriented tympanic membrane (TM) of the patient. Cannula (320) may be then inserted into the ear of the patient. An endoscope or other similar device may be used for visualization of the patient's tympanic membrane (TM) as cannula (320) is inserted through the ear canal. As tip member (322) approaches the patient's TM, cannula (320) may be rotated to fine tune the angle of tip member (322) to position tip member (322) into proper alignment with the patient's tympanic membrane (TM). As can be seen in FIG. 28, cannula (320) may be further advanced such that tip member (322) engages the patient's tympanic membrane (TM) in full apposition. Pushbutton (306) may then be actuated by a user, and the PE Tube (200) may be delivered to the patient's tympanic membrane (TM). In some other exemplary procedures, cannula (320) may be merely flexible and the ear canal may be used to provide a force sufficent to bend cannula (320) such that it may be positioned into alignment with the patient's tympanic membrane (TM). Of course, PETDD (300) may be used in various other ways as will be apparent to those of ordinary skill in the art in view of the teachings herein.

IV. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In some instances, the device is sterilized using conventional ethylene oxide sterilization techniques and systems. In some other instances, the device is placed in a closed and sealed container, such as a plastic or TYVEK bag; and the container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, steam, etc.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An instrument comprising:
a handpiece body;
a shaft assembly extending distally from the handpiece body and rotatable relative to the handpiece body, the shaft assembly including an elongate tube with a plurality of shafts coaxially and slidably disposed therein, the elongate tube having (1) a bendable section that can bend within a plane between a linear state and a bent state, (2) a proximal section disposed proximal to the bendable section and defining a longitudinal axis, and (3) a tip disposed distal to the bendable section and configured to engage a tympanic membrane of a patient;
a thumbwheel coupled to the elongate tube and operable to rotate the elongate tube about the longitudinal axis defined by the proximal section of the elongate tube to change an angle of the tip; and
a drive assembly disposed within the handpiece body that can longitudinally translate the plurality of shafts relative to the elongate tube of the shaft assembly including through the bendable section when the bendable section is in the bent state in a predetermined sequence to at least one of pierce the tympanic membrane or deploy a tympanostomy tube into the tympanic membrane.

2. The instrument of claim 1, wherein the thumbwheel and the shaft assembly form a unitary component.

3. The instrument of claim 1, wherein the bendable section defines a plurality of cutouts extending around a portion of the bendable section such that a solid longitudinally extending member extends along a length of the bendable section.

4. The instrument of claim 3, wherein the bendable section includes a plurality of ribs and the longitudinally extending member, the plurality of ribs and the longitudinally extending member defining the plurality of cutouts.

5. The instrument of claim 1, wherein at least one shaft of the plurality of shafts can maintain a neutral axis throughout the bendable section when the bendable section is in the bent state.

6. The instrument of claim 1, wherein the bendable section of the elongate tube is malleable such that the bendable section can remain in the bent state without a continuously applied force.

7. The instrument of claim 1, wherein at least one of the elongate tube or a shaft of the plurality of shafts includes nylon.

8. The instrument of claim 1, wherein at least one of the elongate tube or a shaft of the plurality of shafts includes polyether ether ketone (PEEK).

9. The instrument of claim 1, wherein the plurality of shafts of the shaft assembly includes at least one of a piercer that can pierce the tympanic membrane or a pusher that can deploy the tympanostomy tube into the tympanic membrane.

10. The instrument of claim 1, wherein lubricant is disposed on at least one surface of at least one shaft of the plurality of shafts.

11. The instrument of claim 1, wherein the tip is configured to engage with the tympanic membrane without requiring significant pressure to be applied against the tympanic membrane.

12. The instrument of claim 1, wherein the tip of the elongate tube is obliquely angled relative to a central axis of the elongate tube.

13. The instrument of claim 1, wherein at least one of a portion of the elongate tube or the tip includes at least one of nylon or polyether ether ketone (PEEK).

14. An apparatus, comprising:
a handpiece body;
a shaft assembly extending distally from the handpiece body and rotatable relative to the handpiece body, the shaft assembly including an elongate tube and a plurality of shafts coaxially and slidably disposed within the elongate tube, the elongate tube having (1) a bendable section that can bend within a plane between a linear state and a bent state, (2) a proximal section disposed proximal to the bendable section and defining a longitudinal axis, and (3) a tip disposed distal to the bendable section and configured to engage a tympanic membrane of a patient;
a thumbwheel coupled to the elongate tube and operable to rotate the elongate tube to move the tip in a path around the longitudinal axis defined by the proximal section of the elongate tube; and
a drive assembly disposed within the handpiece body that can longitudinally translate the plurality of shafts relative to the elongate tube of the shaft assembly in a predetermined sequence to at least one of pierce the tympanic membrane or deploy a tympanostomy tube into the tympanic membrane.

15. The apparatus of claim 14, wherein:
the drive assembly can longitudinally translate at least one shaft of the plurality of shafts relative to the elongate tube including through the bendable section when the bendable section is in the bent state.

16. The apparatus of claim 14, wherein the bendable section defines a plurality of cutouts extending around a portion of the bendable section such that a solid longitudinally extending member extends along a length of the bendable section.

17. The apparatus of claim 14, wherein the thumbwheel and the shaft assembly form a unitary component.

18. The apparatus of claim 14, wherein the thumbwheel is further configured to rotate the elongate tube to change an angle of the tip.

19. An instrument comprising:
a handpiece body;
a shaft assembly including an elongate tube and a plurality of shafts coaxially and slidably disposed within the elongate tube, the elongate tube having (1) a bendable section that can bend within a plane between a linear state and a bent state, (2) a proximal section disposed proximal to the bendable section, and (3) a distal tip configured to engage a tympanic membrane of a patient;
a tympanostomy tube disposed within the elongate tube distal to the bendable section;
a thumbwheel coupled to the elongate tube and operable to rotate the elongate tube to (1) change an angle of the tip and (2) move the tympanostomy tube relative to the proximal section of the elongate tube; and
a drive assembly disposed within the handpiece body that can longitudinally translate the plurality of shafts relative to the elongate tube of the shaft assembly including through the bendable section when the bendable section is in the bent state in a predetermined sequence to at least one of pierce the tympanic membrane or deploy the tympanostomy tube into the tympanic membrane.

20. The instrument of claim 19, wherein the plurality of shafts of the shaft assembly are coupled to the handpiece body for rotation about a central longitudinal axis of the elongate tube, the bendable section of the elongate tube being configured to remain in the bent state during rotation of the shaft assembly about the central longitudinal axis of the elongate tube.

21. The instrument of claim 19, further comprising a pushbutton disposed on the handpiece body and operable to actuate the drive assembly, the thumbwheel disposed distally of the pushbutton.

\* \* \* \* \*

UNITED STATES PATENT AND TRADEMARK OFFICE
CERTIFICATE OF CORRECTION

PATENT NO.         : 10,195,086 B2                                    Page 1 of 1
APPLICATION NO.    : 14/456080
DATED              : February 5, 2019
INVENTOR(S)        : Nga K. Van et al.

It is certified that error appears in the above-identified patent and that said Letters Patent is hereby corrected as shown below:

On the Title Page

Item (54) and in the Specification, Column 1, Line 1, should read --TYMPANOSTOMY TUBE DELIVERY DEVICE WITH ROTATABLE FLEXIBLE SHAFT--

Signed and Sealed this
Sixth Day of August, 2019

Andrei Iancu
*Director of the United States Patent and Trademark Office*